United States Patent [19]

Fuller et al.

[11] Patent Number: 4,829,099

[45] Date of Patent: May 9, 1989

[54] METABOLICALLY ACCEPTABLE POLYISOCYANATE ADHESIVES

[75] Inventors: William D. Fuller, San Diego; Robert K. Blair, Oceanside; Murray Goodman, La Jolla, all of Calif.

[73] Assignee: Bioresearch, Inc., Farmingdale, N.Y.

[21] Appl. No.: 74,597

[22] Filed: Jul. 17, 1987

[51] Int. Cl.$^4$ ............................................. C08G 18/00
[52] U.S. Cl. ................................ 523/111; 128/334 R; 523/118; 524/795; 528/52; 528/53; 528/58; 560/8; 560/81; 560/82; 560/91; 560/103; 560/112; 560/129; 560/190; 560/330; 560/355; 560/358; 560/360
[58] Field of Search ................ 523/111, 118; 524/795; 528/52, 53, 58; 560/8, 81, 82, 91, 103, 112, 129, 190, 330, 355, 358, 360; 128/334 R

[56] References Cited

U.S. PATENT DOCUMENTS 3,437,680  4/1969  Farrissey et al. .................... 560/91

FOREIGN PATENT DOCUMENTS 673757  11/1963  Canada .

*Primary Examiner*—Maurice J. Welsh
*Attorney, Agent, or Firm*—Larson and Taylor

[57] ABSTRACT

Metabolically-acceptable, surgical adhesives are prepared from polyisocyanates having the structral formula:

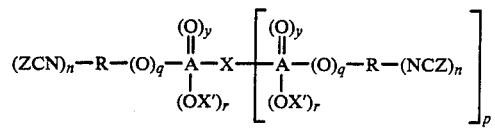

wherein
R is a polyvalent aliphatic radical of about 1 to 10 carbon atoms or a polyvalent aromatic radical of 6 to about 24 carbon atoms;
A is C, S or P;
Z is O or S;
Y is 1 when A is C or P, and 2 when A is S;
n is 1 or 2;
p is at least 1;
q is 0 or 1, with the proviso that when A is carbon or sulfur, q is 0;
r is 0 or 1, with the proviso that when A is carbon or sulfur, r is 0;
X is a residue of an organic compound having active hydrogen-containing groups; and
X' is a residue of an organic compound having at least 1 active hydrogen-containing group.

47 Claims, 1 Drawing Sheet

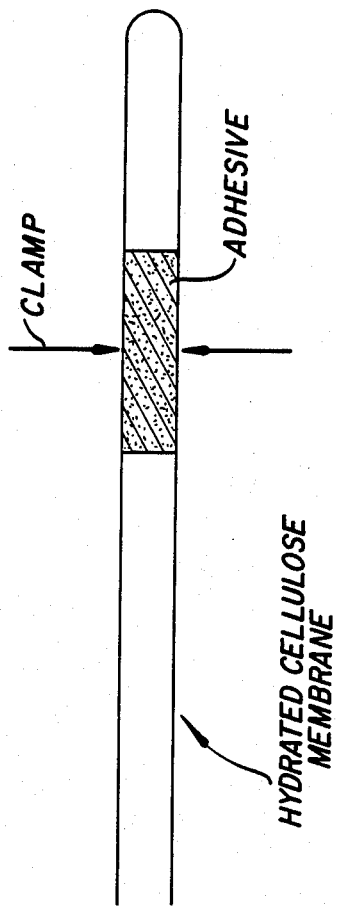

METABOLICALLY ACCEPTABLE POLYISOCYANATE ADHESIVES

BACKGROUND OF THE INVENTION

1. Field of the Invention

This invention relates to adhesives prepared from metabolically-acceptable polyisocyanate or polyisothiocyanate monomers. More particularly, the present invention is concerned with surgical adhesive polymers derived from these polyisocyanate monomers which do not metabolize to toxic products.

2. Brief Description of the Prior Art

In recent years there has developed increased interest in replacing or augmenting sutures with adhesive bonds. The reasons for this increased interest are many but those most evident are:

(1) the potential speed with which repair might be accomplished;

(2) the ability of a bonding substance to effect complete closure, thus preventing seepage of fluids;

(3) the possibility of forming a bond without excessive deformation of tissue, and (4) possible improvement in repair of tissue too weakened by disease or age to permit effective suturing.

Studies in this area, however, have revealed that, in order for surgical adhesives to be accepted by surgeons, they must possess a number of properties. First, they must exhibit high initial tack and an ability to bond rapidly to living tissue. Secondly, the strength of the bond should be sufficiently high to cause tissue failure before bond failure. Thirdly, the adhesive should form a bridge, preferably a permeable flexible bridge. Fourthly, the adhesive bridge and/or its metabolic products should not cause local histotoxic or carcinogenic effects.

A number of adhesive systems such as alkyl cyanoacrylates, polyacrylates, maleic anhydride/methyl vinyl ethers, epoxy systems, polvinyl alcohols, formaldehyde resins and isocyanates have been investigated as possible surgical adhesives. None has gained acceptance because each fails to meet one or more of the criteria noted above. The principal criticism of these systems has been the potential toxicity problems they pose. In the case of adhesives based on conventional isocyanates, for example, the production of aromatic and aliphatic diamines by metabolism could lead to local histological reactions at minimum, and possibly to even more serious systemic toxicity.

It is an object of the invention to provide novel metabolically-acceptable polyisocyanate adhesives, including polyisothiocyanate-based adhesives and in particular metabolically-acceptable surgical adhesives.

Yet another object of the invention is to provide metabolically-acceptable surgical adhesives which are biodegradable.

A further object of the invention is to provide a method for closing wounds in living tissue by use of novel, metabolically-acceptable surgical adhesives.

An additional object of the invention is to provide metabolically-acceptable adhesives low in toxicity as a consequence of their physical properties.

SUMMARY OF THE INVENTION

These and other objects of the invention are obtained by using a curable, surgical adhesive comprised of:

A. a metabolically-acceptable polyisocyanate (including polyisothiocyanates) having the structural formula:

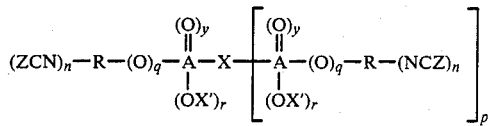

wherein

R is a polyvalent aliphatic radical of about 1 to 10 carbon atoms or a polyvalent aromatic radical of 6 to about 24 carbon atoms;

A is carbon, sulfur or phosphorus;

Z is oxygen or sulfur;

y is 1 when A is carbon or phosphorus, and 2 when A is sulfur;

n is 1 or 2;

p is at least 1;

q is 0 or 1, with the proviso that when A is carbon or sulfur, q is 0;

r is 0 or 1, with the proviso that when A is carbon or sulfur, r is 0;

X is a residue of an organic compound having active hydrogen-containing groups; and X' is a residue of an organic compound having at least 1 active hydrogen-containing group; or B. an excess of said polyisocyanate A in admixture with an organic compound containing at least two active hydrogen atoms reactive with isocyanate groups of polyisocyanate A.

The polyisocyanates or polyisothiocyanates of the invention, polymeric products of these monomers per se and polymeric reaction products of the monomers and organic compounds containing reactive hydrogen atoms, are found to be metabolically-acceptable, that is, incapable of breaking down into toxic materials such as aromatic or aliphatic diamines. Rather, the compounds of the invention are characterized by their metabolism into innocuous materials such as amino acids.

It should be understood that for purposes of convenience both the novel polyisocyanates and polyisothiocyanates of the invention will be referred to in the specification and claims simply as "polyisocyanates".

In the structural formula of the polyisocyanates of the invention, illustrative of suitable R radicals are divalent or polyvalent aliphatic radicals, which may be straight-chain or branched, such as methylene, 1,2-ethylene, 1,2-propylene, 1,3-propylene, 1,2,butylene, 1,3-butylene, 1,4-butylene, 2,3-butylene, 1,4-pentylene, 1,5-pentylene, 2,4-pentylene, 1,6-hexylene, 1,7-heptylene, 1,8-octylene, 2,6-octylene, 1,9-nonylene, 1,10-decylene, vinylene, propenylene, 2-butenylene, 2-methyl-1-butenylene, 3-methyl-2-pentenylene, butadienylene, etc.; divalent or polyvalent cycloaliphatic radicals, such as 1,3-cyclopentylene, 1,3-cyclohexylene, 1,4-cyclohexylene, 1,2,4-cyclopentylene, 1,3,4-cyclohexylene; divalent and polyvalent aralkyl radicals, such as benzyl, 3-phenylpropyl, diphenylmethyl, etc.; and divalent or polyvalent aromatic radicals, such as para, meta and ortho-phenylene, biphenylene and the like.

The radical "X" in the novel polyisocyanates of the invention can be the residue of any organic compound, which contains active hydrogen-containing groups as determined by the Zerewitinoff method. Such active hydrogen-containing compounds include, for example, compounds having at least hydroxyl groups, thiol groups and the like. Thus, by way of illustration, the radical "X" can be the residue of simple hydroxyl- or thiol-group terminated alkanes, which may be straight-chain or branched, aralkanes, etc., as well as polymeric radicals such as hydroxy or thiol-group terminated polyesters, polyethers, polythioethers, polyacetals, polycarbonates, polyanhydrides, polyphosphates, polyphosphazines, polypeptides, polydepsipeptides, polyamides, polyester-polyether block copolymers and the like. In most instances, the compounds and/or polymers will contin at least two functional groups, often up to 8 functional groups and will have a molecular weight of 50 to 10,000, more often about 100 to 1,000.

The hydroxyl-group-containing polyesters may be, for example, reaction products of polyhydric alcohols, preferably dihydric alcohols and polybasic, preferably dibasic, carboxylic acids. The corresponding polycarboxylic acid anhydride or corresponding polycarboxylic acid esters of lower alcohols or their mixtures may be used instead of the free polycarboxylic acids for preparing the polyesters. The polycarboxylic acid may be aliphatic, cycloaliphatic, aromatic and/or heterocyclic and may be substituted, e.g. with halogen atoms or may be unsaturated. Examples include succinic acid, adipic acid, suberic acid, azelaic acid, sebacic acid, phthalic acid, terephthalic acid, isophthalic acid, trimellitic acid, tetrahydrophthalic acid, hexahydrophthalic acid, tetrachlorophthalic acid, glutaric acid, maleic acid, fumaric acid. Any suitable polyhydric alcohol may be used, such as, for example, ethylene glycol; propylene-1,2- and -1,3-glycol; butylene-1,4- and -2,3-glycol; hexane-1,6-diol; octane-1,8-diol; neopentyl glycol; cyclohexanedimenthol; 1,4-bis-hydroxymethylcyclohexane; 2-methyl-propane-1,3-diol; glycerol; trimethylolpropane; hexane-1,2,3-triol; butane-1,2,4-triol; trimethylolethane; pentaerythritol; ribose; erythose, quinitol; mannitol; sorbitol; glucose; starches; fructose; cane sugar; dextrans; castor oil; methylglycoside; diethylene glycol; triethylene glycol; tetraethylene glycol; polyethylene glycols; dipropylene glycol; polypropylene glycols; dibutylene glycol and polybutylene glycols. The polyesters may also contain a proportion of carboxyl end groups. Polyesters of lactones such as caprolactone, or hydroxycarboxylic acids such as hydroxycaproic acid may also be used. The hydroxyl-terminated polyesters include hydroxyl-terminated polyorthoesters such as are prepared by the melt polymerization of 2,2-diethoxytetrahydrofuran with diols.

Suitable polyhydric polyalkylene ethers (polyethers) include, for example, the polymerization product of an alkylene oxide beginning with any suitable initiator. The initiator may be a difunctional compound, including water, so that the resulting polyether is essentially a chain of repeating alkyleneoxy groups as in polyethylene glycol, polypropylene glycol, polybutylene glycol and the like; or the initiator may be any suitable active hydrogen containing compound which may be a monomer or even a compound having a relatively high molecular weight including other active hydrogen containing compounds as disclosed herein. Any suitable alkylene oxide may be used such as, for example, ethylene oxide, propylene oxide, butylene oxide, amylene oxide, tetrahydrofuran, epihalohydrins such as epichlorohydrin, dioxalane, styrene oxide and the like. Suitable initiators include, for example, water, polyhydric alcohols, preferably having 2 to 8 hydroxyl groups, amines, preferably having 2 to 8 replaceable hydrogen atoms bonded to nitrogen atoms and the like to which the alkylene oxides may be added. The resulting polyhydric polyalkylene ethers may have either primary or secondary hydroxyl groups or mixtures of primary and secondary hydroxyl groups. It is preferred to use alkylene oxides which contain from 2 to 5 carbon atoms and, generally speaking, it is advantageous to condense from about 1 to about 30 equivalents of alkylene oxide per functional group of the initiator. Specific examples of initiators are water, ethylene glycol, propylene glycol, glycerol, trimethylolpropane, pentaerythritol, arabitol, sorbitol, maltose, sucrose, ammonia, diethanolamine, triethanolamine, dipropanolamine, tripropanolamine, diethanolpropanolamine, tributanolamine, 2,4-tolylenediamine, 4,4'-diphenylmethanediamine, 4,4',4''-triphenylmethanetriamine, ethylenediamine, propylenediamine, propylenetriamine, N,N,N',N'-tetrakis-(2-hydroxy-propyl)-ethylene diamine, diethylene triamine and the like. There are many suitable processes for the preparation of polyhydric polyalkylene ethers including U.S. Pat. Nos. 1,922,459; 3,009,939 and 3,061,625 or by the process disclosed by Wurtz in 1859 and discussed in the Encyclopedia of Chemical Technology, Volume 7, p. 257 to 262, published by Interscience Publishers, Inc. (1951).

By "polythioethers" are meant, in particular, the condensation products of dithioglycol with itself and/or with other glycols, dicarboxylic acids, formaldehyde, or analogous polymers synthesized from ethylene sulfide, etc. The products obtained are polythio-mixed ethers or polythioether esters, depending on the co-component.

Hydroxyl-terminated polyester-polyether block copolymers can be derived from polyalkylene glycols and hydroxyacids such as glycolic, lactic and hydroxycaproic acid by the melt polymerization of the polyalkylene glycol with the corresponding hydroxyacid or its cyclic lactone (e.g. glycolide, lactide, caprolactone, etc.).

The polyacetals may be, for example, the compounds which may be obtained from glycols, e.g. diethylene glycol, triethylene glycol, 4,4'-dihydroxydiphenyldimethylmethane, hexanediol, etc. and formaldehyde. Suitable polyacetals may also be prepared by the polymerization of cyclic acetals.

The polycarbonates with hydroxyl groups may be of the known kind, e.g. those which may be prepared by reacting diols, such as propane-1,3-diol, butane-1,4-diol and/or hexane-1,6-diol or diethylene glycol, triethylene glycol or tetraethylene glycol, with diarylcarbonates such as diphenylcarbonate or with phosgene.

Mixtures of any of the compounds of any of the classes set forth hereinbefore may be used and such compounds may also contain other substituents including halogen atoms such as, for example, chloro, bromo, iodo and the like; nitro groups; alkoxy radicals such as, for example, methoxy, ethoxy, propoxy, butoxy and the like; carboalkoxy groups such as, for example, carbomethoxy, carbethoxy and the like; dialkylamino groups such as, for example, dimethylamino, dipropylamino, methylethylamino and the like; carbonyl, thiocarbonyl, phosphoryl, phosphato and like groups.

Of the various monomeric and polymeric residues that can constitute the radical "X" in the isocyanates of the invention those generally preferred are selected from the following structures:

Polyether

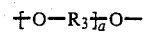

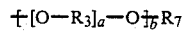

Polyester

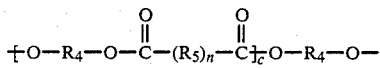

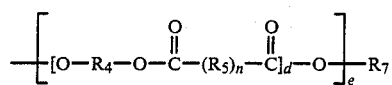

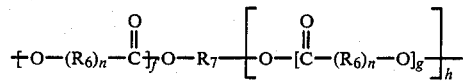

Polyether/Polyester Copolymers

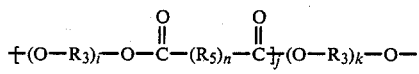

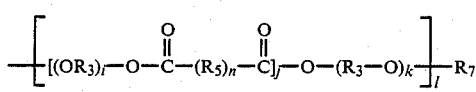

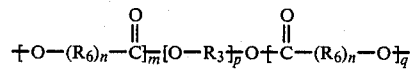

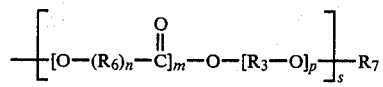

wherein $R_3$, $R_4$, $R_5$, and $R_6$ are aliphatic radicals of 1 to 12 carbon atoms, which may be straight-chain or branched, or aromatic radicals of 6 to 12 carbon atoms including oxygen-bridged aliphatic and aromatic radicals; $R_7$ is a polyfunctional active hydrogen-containing aliphatic radical; a, b, c, d, f, g, h, i, j, k, m, p, and q are integers of at least 1 usually up to 10 or more; b, e, l, and s are integers of at least 2 usually 3 or more; and n is an integer of 0 or 1.

The novel polyisocyanates and polyisothiocyanates of the invention are film-forming materials that may be prepared in numerous ways as, for instance, by the phosgenation or thiophosgenation of polyamine compounds having the structure:

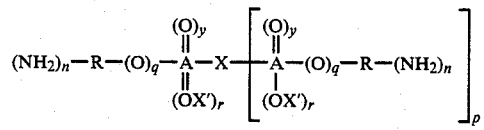

wherein n, R, A, y, q, r, p, X, and X' are as defined above. These polyamine precursors may be prepared by any one of many possible condensation methods, well-known to someone skilled in the art, of an appropriate carboxylic, phosphorus or sulfonic acid derivative with the active hydrogen containing radicals "X", as defined above. A convenient route when R is an aromatic group, involves reacting one mole of a compound having 2 terminal active hydrogen-containing groups with 2 moles of a nitro-substituted compound having the structure:

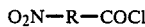

or

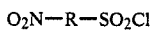

or

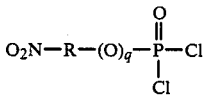

wherein R is aromatic and defined as above and q is 0 or 1. These condensation reactions may be carried out "in the melt", i.e. by heating the mixture of the reactants in the absence of a solvent; or in an inert solvent such as toluene, tetrahydrofuran, benzene, dioxane, etc. The nitro compounds are then reduced to the corresponding amines which are subjected to phosgenation. These syntheses can be represented as follows, using for purposes of illustration hydroxy-terminated compounds as the organic compound having terminal active hydrogen atoms.

Scheme I

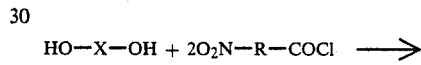

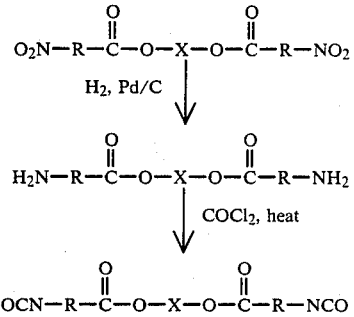

Scheme II

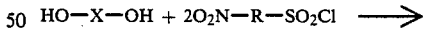

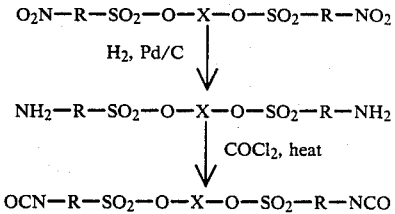

wherein R and X are as defined above.

The reduction and phosgenation or thiophosgenation steps in these syntheses can be carried out using any of the well-known techniques. For instance, the reduction can be effected by simple hydrogenation in the presence of a suitable hydrogenation catalyst such as palladium, or by transfer hydrogenation. The phosgenation or thiophosgenation can be carried out by either a cold phase-hot phase phosgenation or by they hydrochloride process wherein the corresponding amine hydrochloride is phosgenated. The phosgenation can be carried out continuously or intermittently and inert solvents such as dioxane, chlorobenzene, o-dichlorobenzene, tetrahydrofuran, etc., are preferably employed for the reaction. Phosgene is conveniently stored as a stable solution in most of the above-mentioned solvents.

In an alternate procedure, especially useful for the synthesis of polyamines in which the groups R are aliphatic, an amino acid may be condensed with an active hydrogen-terminated compound by suspending the reactants in an inert solvent, such as toluene, chlorobenzene or benzene. The mixture is heated under reflux and hydrogen chloride gas passed in a continuous stream through the mixture. The water of condensation is removed by azeotropic distillation from the reaction mixture in order to drive the reaction to completion, i.e.,

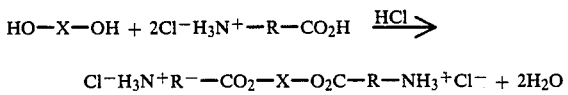

The hydrochloride salt of the polyamine may be phosgenated or thiophosgenated in the usual manner to give the polyisocyanate or polyisothiocyanate.

An alternate procedure for the synthesis of these polyamine precursors involves the condensation of suitably-protected amino acid derivatives with an active hydrogen-containing compound, i.e.,

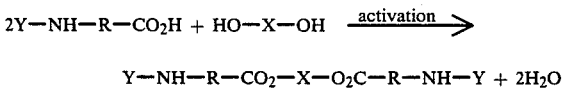

Any suitable, selectively-cleavable amine-protecting group Y, well-known to someone skilled in the art, may be used for this purpose. For example, Y may be benzyloxycarbonyl or t-butyloxycarbonyl. In this method, the protected amino acid derivative is condensed with the active hydrogen-containing compound through use of suitable activation techniques. There are many activation methods known, for instance, coupling agents such as carbodiimides, 1,1-carbonyldiimidazole, the intermediate formation of symmetrical or mixed anhydrides, active esters and the like, all of which will be well-known to someone skilled in the art. The most preferred methods involve the use of 1,1-carbonyldiimidazole or mixed carboxylic-carbonic anhydrides, catalyzed by suitable catalysts such as pyridine or 4-dimethylaminopyridine.

The protected polyamine precursors may be deprotected by appropriate procedures. For example, when Y is benzyloxycarbonyl, the compounds may be:

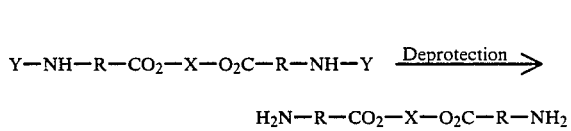

deprotected by catalytic hydrogenolysis or under anhydrous, acidic conditions, for example using solutions of hydrogen bromide in glacial acetic acid. Alternatively, when the t-butyloxycarbonyl group is used for amine protection, cleavage may be effected selectively using anhydrous acids, such as trifluoroacetic acid or solutions of hydrogen chloride in anhydrous dioxane. The resulting polyamines are phosgenated or thiophosgenated by the usual procedures, as outlined above.

Exemplary of preferred metabolically-acceptable diisocyanates of the invention are those having the structure:

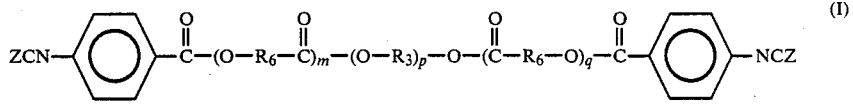

wherein m and q are 1 to about 10 or more; p is 1 to 20; $R_3$ and $R_6$ are aliphatic or aromatic radicals having 1 to 12 carbon atoms and Z is oxygen or sulfur. Of these diisocyanates, particularly preferred are those having the structure:

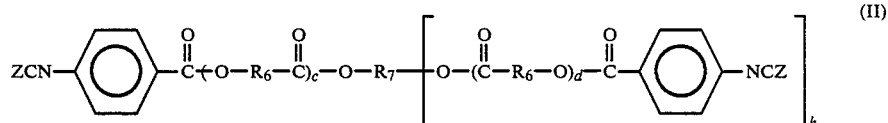

wherein m and q are 2 or 4 and p is 4 to 20. These monomers, for example, will degrade ultimately to the metabolically-acceptable products, p-aminobenzoic acid, polyethylene glycol, and glycolic acid, all of which are innocuous. Other preferred metabolically-acceptable polyisocyanates include those having the structure:

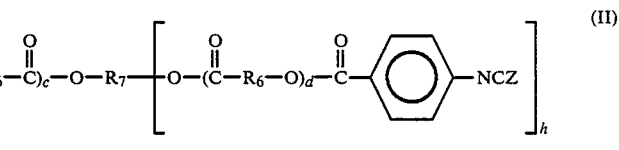

wherein $R_6$ is an aliphatic or aromatic radical having 1 to 12 carbon atoms; $R_7$ is a polyfunctional active hydrogen-containing aliphatic radical; c, d, and h are integers of at least 1; and Z is oxygen or sulfur. Of these polyisocyanates, particularly preferred are those having the structure:

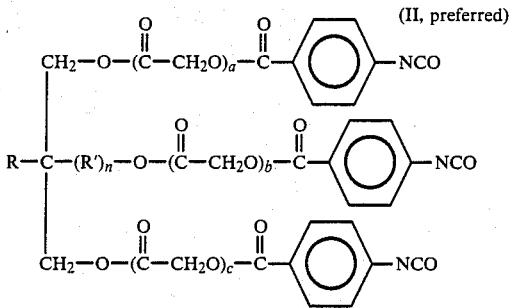

(II, preferred)

wherein
a+b+c is at least 3;
R is hydrogen or a lower alkyl;
R' is an alkylene of 1 to 4 carbon atoms; and
n is an integer of 0 or 1.

These monomers, for example, will degrade ultimately to the metabolically-acceptable products, p-aminobenzoic acid, glycerol or related triol and glycolic acid, which are innocuous.

A preferred curable adhesive composition of the invention is comprised of a mixture of 5 to 95% by weight of polyisocyanate I and 95 to 5% by weight of polyisocyanate II.

The novel polyisocyanates of the invention have large variations in physical properties and may be used alone or in admixture with dissimilar polyisocyanates of the invention. Consequently, control over the physical properties of the polyisocyanate formulation and the polymer formed after set-up are achieved in three ways:

(1) Variations in the parameters a, b, c, m, p, q, R and R';

(2) Variations of polyisocyanates, particularly admixtures of polyisocyanates of Structure I with polyisocyanates of Structure II.

(3) Using combinations of 1 and 2.

These characteristics allow for control of physical properties of the adhesive bridge which is formed. For instance, the absorption rate of the bridge may be controlled, the flexibility of the bridge may be controlled (a flexible bridge being preferred) and the porosity of the bridge can be controlled. In many cases, the polyisocyanates of the invention or mixtures thereof can be used as single component adhesive systems which cure rapidly upon exposure to surface moisture. Alternatively, two component adhesive systems can be formulated with the polyisocyanates of the invention. In the manufacture of two component adhesive systems the polyisocyanate or admixture of polyisocyanates and a curing agent are maintained separately until just prior to use. Suitable curing agents including conventional polyfunctional compounds such as glycerol, inositol, 1,4-butane diol, trimethylolpropane, neopentylglycol, methylene dianiline, phenyldiethanolamine, triisopropanolamine, pentaerythritol and the like. Alternately, the active hydrogen-containing polymeric components, H—X—H, derived from the radical "X" discussed above, may be used as curing agents. Also useful as curing agents are the amines described above.

It may be desirable in both a single component adhesive system and a two component adhesive system to include a catalyst so as to speed up the curing reaction. Any conventional catalyst used in urethane production can be used as, for example, tertiary amines such as 1,2,4-trimethyl piperazine, N-methylmorpholine, triethylamine, tri-n-butylamine N-(N,N-dimethylaminopropyl)-2-pyrrolidone, 2,4,6-collidine, pyridine, quinaldine, triethanolamine, 4-dimethylaminopyridine, tris-2,4,6-(dimethylaminomethyl)phenol and the like and tin compounds such as tin hexanoate, tri-n-butyl tin acetonate, di-t-butyl tin dilaurate, stannous-2-ethyl hexanoate and the like. Further preferred curing agents include diamines of the corresponding polyisocyanate, i.e., compounds of the same structure as the polyisocyanate but possessing amine groups instead of isocyanate groups. Mixtures of one or more amines, one or more tin compounds and admixtures of both tin compounds and amines can be used as catalysts for the reaction. In fact, in some cases a synergistic result is found when a combination of catalysts is employed. A preferred combination is 1,2,4-trimethylpiperazine/triethanolamine.

Other preferred catalysts for use in the reaction are:
I. Pyridine carboxylates having the structure:

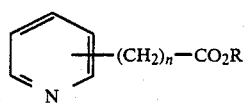

wherein
R is lower alkyl; and
n is 0 to 6 or more, such as the nicotinate esters (n=0) and pyridylacetate esters (n=1).

Exemplary of such catalysts are 3-methyl or 3-ethyl nicotinate and ethyl 3-pyridylacetate.

II. Saturated, aliphatic analogs of pryridine carboxylates having the structure:

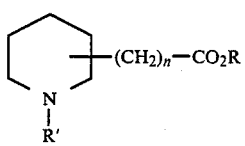

wherein
R and R' are lower alkyl; and
n is 0 to 6 or more. Exemplary is ethyl 1-methyl-nipecotate.

III. Aliphatic amine catalysts having the structure:

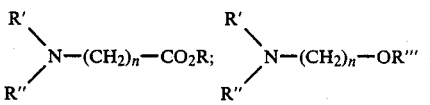

wherein
R, R' and R" are lower alkyl; and
n is 1 to 6 or more and R''' is H or

Exemplary is 2-(N,N-dimethylamino)-ethyl acetate.

In all instances, catalyst is used in an amount sufficient to speed the reaction and generally in an amount of from about 0.05 to 30 parts by weight based on 100 parts by weight of the polyisocyanate.

Adhesive solutions of the polyisocyanates of the present invention can be prepared, if desired, by dissolving the polyisocyanate in typical adhesive solvents including ethers having 4–6 carbon atoms such as tetrahydrofuran, dioxane, 1,2-dimethoxyethane and diisopropyl ether; ketones having 3–7 carbon atoms such as acetone, methyl ethyl ketone, methyl isobutyl ketone and diisopropyl ketone; N,N-dialkyl lower amides containing 3–6 carbon atoms such as dimethyl formamide, dimethyl acetamide, diethylacetamide and N,N-diethyl formamide and sulfones and sulfoxides having 2–4 carbon atoms such as dimethyl sulfoxide and tetramethylene sulfone. Also useful solvents are trifluoroethanol and trimethylphosphate. Alkyl substituted benzenes such as toluene and xylene can be used in admixture with the above solvents. Preferred solvents are methylene chloride and fluorinated halogenated hydrocarbons such as trichlorofluoromethane; dichlorodifluoromethane, chlorotrifluoromethane, chlorodifluoromethane, 1,1,2-trifluoroethane and sym-dichlorotetrafluoroethane. Particularly preferred is dichlorofluoromethane.

The polyisocyanates of the invention can be reacted with any of the polyfunctional organic compounds normally used for polyurethane formation to form curable prepolymers and higher molecular weight adhesives. Generally speaking, any compound having an active hydrogen atom which will react with an -NCO group may be used. Illustrative of such compounds are the simple and polymeric esters, ethers, esterethers, amides, esteramides, thioethers, acetals, carbonates, diamines, anhydrides, phosphates, phosphazines, peptides, including retroinversopeptides, and the like, and any combination or block copolymers of the above. In addition, any suitable aliphatic polyol may be used as, for example, alkane diols including, for example, ethylene glycol, butylene glycol, 1,3-butylene glycol, 1,5-pentane diol, 1,4-butane diol, 1,3-pentane diol, 1,6-hexane diol, 1,7-heptane diol, 2,2-dimethyl-1,3-propane diol, 1,8-octane diol, 1,20-eicosane diol and the like; alkene diols such as, for example, 1-butene-1,4-diol, 1,3-butadiene-1,4-diol, 2-pentene-1,5-diol, 2-hexene-1,6-diol, 2-heptene-1,7-diol and the like; alkyne diols such as, for example, 2-butyne-1,4-diol, 1,5-hexadyne-1,6-diol and the like; alkane triols such as, for example, glycerol, 1,3,6-hexanetriol, 1,3,7-heptanetriol, 1,4,8-octane triol, 1,6,12-dodecane triol and the like; alkene triols such as 1-hexene-1,3,6-triol and the like; alkyne triols such as 2-hexyne-1,3,6 triol and the like; alkane tetrols such as, for example, 1,2,5,6-hexane tetrol and the like; alkene tetrols such as, for example, 3-heptene-1,2,6,7-tetrol and the like; alkyne tetrols such as, for example, 4-octyne-1,2,7,8-tetrol or any admixtures, block, or random copolymers derived from the above.

Also contemplated for use as curing agents are dioximes or polyoximes. These compounds both act as conventional curing agents and also confer added hydrolytic instability on the adhesives because of the susceptibility of "oximinourethanes" to aqueous hydrolysis (see below). While the isocyanates of the invention normally result in adhesives which are metabolized in vivo in another embodiment of the invention, biodegradable polymers useful as absorbable surgical adhesives can be prepared by selecting for reaction with the metabolically-acceptable polyisocyanates a polyfunctional compound which contains hydrolyzable linkages and/or linkages susceptible to cleavage by enzymes such as endogenous proteolytic enzymes. For example, in the case of a diol monomer, block polyether-polyester copolymers (III) derived from polyethylene or propylene glycols or copolymers, copolymerized with ester monomers such as glycolide, lactide, caprolactone, etc. are useful for preparing urethane adhesives with a range of hydrolysis rates.

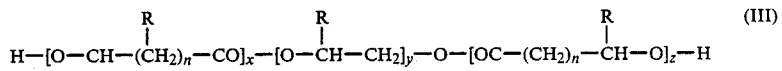

(III)

The rate of hydrolysis of the resultant adhesive may be controlled through variation of the hydrophobic/hydrophilic balance in the diol monomers III.

Other diol monomers which can be reacted with the novel isocyanates for the preparation of absorbable adhesives include orthoester monomers of the type (IV), prepared from, for example, the copolymerization of 2,2-diethoxytetrahydrofuran (n=3) and a wide variety of diols.

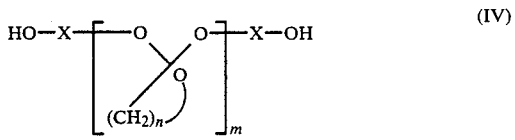

(IV)

The diols may be simple, such as alkyl diols, or complex structures, such as the block copolymers III. Clearly, a wide variety of structures are conceivable, leading to a broad range of hydrolysis rates for the adhesives.

Diol monomers derived from peptides (e.g. those containing serine) and depsipeptides (copolymers of amino and hydroxy acids) are also useful for the preparation of absorbable adhesives. For example, the peptide diol monomers (V) are susceptible to cleavage by proteolytic enzymes, as would

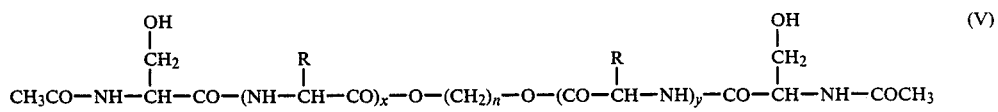

(V)

be similar monomers of the depsipeptide type. Adhesives derived from such monomers are therefore susceptible to cleavage by endogenous proteolytic enzymes.

Also useful for reaction with the novel polyisocyanates of the invention to produce absorbable adhesives are the simple and complex dioximes having the structure:

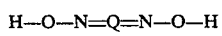

wherein Q is selected from substituted or unsubstituted aliphatic (including cycloaliphatic) or aromatic radicals of 2 to 12 carbon atoms or a polyester, polyesterpolyether block copolymer or polyamide radicals such as described above with reference to the radical "X".

The oximes are excellent nucleophiles which react extremely rapidly with isocyanates to produce "oximinourethanes" that are water-sensitive. The oximes, therefore, render polyisocyanate adhesives into which they are incorporated biodegradable because of the lability of the "oximinourethane" linkage.

The polymers are water-sensitive and their rate of degradation may be controlled through the structure of the reactants. In general, polymers which are derived from aliphatic dioxime monomers are more labile than those derived from aromatic monomers.

Illustrative of simple oxime monomers are:

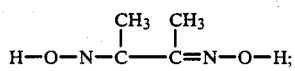

and

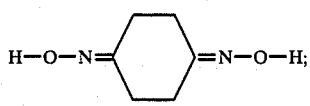

and

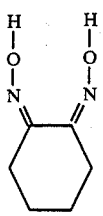

Illustrative of complex dioxime monomers are those prepared by the condensation of a diol with the appropriate methyl keto acid, followed by reaction with hydroxylamine to form the oxime. The following oxime is exemplary:

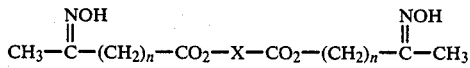

Another example of a complex oxime is the oxime-terminated polyethers synthesized by oxidation of low molecular weight polyethylene glycols, followed by condensation with hydroxylamine. Such complex oximes are exemplified by the following compounds:

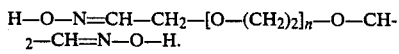

The adhesives of the invention can be applied either as a single component system or as a two component system. In the single component procedure the monomer, with or without catalyst, is applied directly to the tissues to be bonded together. In the two component procedure an excess of isocyanate is reacted with the polyfunctional active hydrogen-containing reactant, i.e. curing agent, to prepare an isocyanate-terminated prepolymer which may be mixed with a catalyst, if required, immediately prior to application to the tissues to be bonded. The molar ratio of NCO groups to active hydrogen functional groups (e.g. hydroxyl, amino, thio, etc. and mixtures thereof) is generally on the order of 2:1 to 4:1 but may be as great as 10:1 or more.

Thus, the invention contemplates an article of manufacture comprised of a two container pack wherein the curable, sterile polyisocyanate (Component A) as described above, is placed in a first container and the polyfunctional organic compound (Component B) containing at least two reactive hydrogen atoms reactive with isocyanate groups of said Component A is placed in a second container. The amount of Component A in the first container will be in excess of Component B in the second container so that the two component system will be ready for mixing and application at the site of the wound-closing. Advantageously, catalysts such as described above for speeding up the curing reaction can be added to the components of either container, but preferably to the curing agent. It should be understood that the components in said first and second container are always maintained in a stable condition prior to admixture.

The preferred adhesives of the invention, however, are single component systems of the polyisocyanate monomer, preferably catalyzed, which react with water to form strong bonding, porous, adhesive bridges. The reaction mechanism is not understood in its entirety but in large part is believed to involve the following sequence of reactions:

First, the water reacts with the isocyanate groups to form a carbamic acid which is unstable and immediately breaks down to an amine and carbon dioxide. The amine reacts with isocyanate to form polyurea which foams due to the simultaneous evolution of carbon dioxide thereby forming a porous, polymeric bridge.

This reaction can be represented as follows:

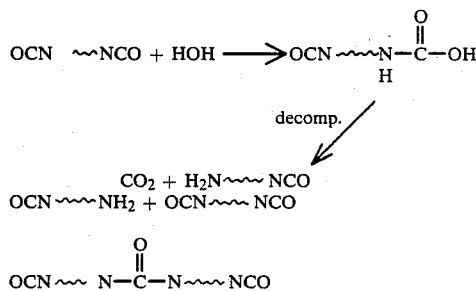

Exemplary of a preferred adhesive is a formulation comprised of 60% by weight of polyisocyanate (I, preferred) wherein m=2; q=2, and p=13 and 40% by weight of polyisocyanate (II, preferred) above wherein a, b, and c are 2, R=H, and n=0. The adhesive is conveniently used as a solution in dichlorofluoromethane (either as a spray or as concentrated drops) and catalyzed as described above. A strong, porous, flexible bond is formed in one to two minutes after application of the adhesive on living tissue.

It has been found that the foregoing adhesive and other formulations of polyisocyanate I and polyisocyanate II form a putty-like bridge which adheres at the wound site and follows and conforms to the movement of tissue without tearing away. The adhesive film or bridge offers no resistance to flexion or change in the tissue to which it adheres but rather conforms to the dynamic movement of the tissue.

The polyisocyanates and polyisothiocyanates of the present invention are preferably sterilized prior to use as surgical adhesives. The sterilization may be effected by use of conventional gaseous sterilizing agents such as ethylene oxide in the absence of moisture. Alternatively, the curable adhesives may be sealed in containers free of moisture and then sterilized by using heat and radiation including X-rays, gamma rays, electrons, neutrons, etc.

The adhesive system of the invention may be applied in any convenient manner as by brushing, spraying, pouring and the like. A preferred method of application is spraying either as a two component system wherein the catalyst and monomer are kept separate until just before application or alternatively as a single component system wherein the catalyst and monomer are premixed and stored in a stable environment until spray application. Another preferred method of application is to deliver to the site drops of the catalyst and monomer, either premixed or separately. If desired, the adhesive composition of the invention may be provided with polymerization inhibitors such as sulfur dioxide.

Not only are the polyisocyanates of the invention characterized by their lack of toxicity when used in vivo, but they also set up extremely rapidly to give stronger bonds than healthy living tissue. Consequently, the polyisocyanates and polyisothiocyanates form strong, useful bonds to all kinds of living tissues so that use of conventional sutures may be eliminated. Also the polyisocyanates of the invention react with moisture on tissue surfaces to form a carbamic acid which breaks down during curing to evolve carbon dioxide gas. The carbon dioxide gas evolution that occurs during the polymerization reaction results in a porous foam-like bridge which by its increased permeability and absorbability is not characterized by the toxicity normally associated with solid continuous adhesive films. The porous permeable nature of the resulting adhesive bridge facilitates transport of essential nutrients into and through the bridge permitting tissue ingrowth and thereby accelerating the wound healing process. Thus, if desired, the polyisocyanate of the invention may include as addenda conventional surface active agents to control foam or bubble size formation in the resulting adhesive bridge.

The compounds of the invention also form very strong bonds to other substrates, providing traces of moisture are present. For this reason, model systems of hydrated cellulose membrane and rat skin were chosen for the purpose of obtaining comparative in vitro data on adhesive monomers and compositions, as set forth in the examples discussed below.

The following examples are included to further illustrate the invention and are not to be considered as limiting the invention in any way.

EXAMPLE 1

Bis-(4-Isocyanatobenzoyl)-Tetraethylene Glycol

A. p-Nitrobenzoyl chloride (390 g. 2.1 mole) and tetraethylene glycol (194 g, 1.0 mole) were dissolved in dry tetrahydrofuran (1 l) and the mixture evaporated under reduced pressure. The resulting thick oil was stirred under high vacuum (0.5 mm) overnight, during which time the mixture solidified. The mixture was slowly heated to 60° C. and maintained at this temperature for 5 hours. On cooling, the product was dissovled in ethyl acetate (2 l), saturated aqueous sodium bicarbonate (2 l) added and the mixture stirred at room temperature for 24 hours. The phases were separated, the organic phase washed with saturated sodium bicarbonate (3×), dried (MgSO$_4$), filtered and the filtrate evaporated to dryness under reduced pressure. The residue was crystallized from ethyl acetate/hexanes to give bis-(4-nitrobenzoyl)-tetraethylene glycol (406 g), m.p. 57.5°–58.5° C., which was homogeneous by TLC.

B. Bis-(4-nitrobenzoyl)-tetraethylene glycol (130 g, 0.264 mole) was dissolved in dry, redistilled ethyl acetate (1.2 l) in a 3-liter, round-bottom flask, palladium on carbon (10%, 7 g) added and the mixture stirred under an atmosphere of hydrogen. The gas was taken up at the rate of approximately 15 l per hour and external ice-cooling was applied periodically to maintain a temperature of 40° C. After hydrogen uptake was complete (35 l), the mixture was stirred at room temperature under hydrogen for two hours. The catalyst was removed by filtration and the filtrate concentrated in vacuo. The product was light and $O_2$ sensitive and was therefore crystallized in the absence of both by addition of hexanes to give bis-(4-aminobenzoyl)-tetraethylene glycol (105 g), m.p. 85°–86.5° C. as a white solid which was homogeneous by TLC.

C. Bis-(4-aminobenzoyl)-tetraethylene glycol (120 g, 0.278 mole) was dissolved in dry dioxane (2.5 l) in a 5-liter, 3-neck flask, equipped with a reflux condenser, drying tube and mechanical stirrer. The solution was stirred vigorously and purged with argon before adding a solution of phosgene in toluene (3M, 650 ml). The mixture was heated slowly to reflux over 2 hours and refluxed for a further 3 hours. The condenser was then rearranged for distillation and solvent removed by distillation at atmospheric pressure until the volume of the reaction mixture was reduced to approximately one third. The reaction mixture was allowed to cool to room temperature under argon and then evaporated under reduced pressure. The residue was re-evaporated several times from dry dioxane to give bis-(4-isocyanatobenzoyl)-tetraethylene glycol (125 g) as a pale yellow, viscous oil which crystallized on prolonged standing at −15° C., m.p. 34°–35° C.

EXAMPLE 2

In Vitro Testing Procedure for Adhesives

Test strips were prepared by cutting regenerated cellulose dialysis membrane into strips (0.5×6 inch) which were boiled with aqueous EDTA (0.2M) for 5 hours. On cooling, the strips were washed thoroughly with distilled water, excess water removed by mopping and the resulting hydrated cellulose samples stored in a 100% humidity chamber.

Adhesive samples were prepared by thoroughly mixing the components (isocyanate monomer, curing agent, if used and catalyst) in the specified ratio. A thin film of the sample was spread on one side of the test strip, which had been folded in half, and the strip then clamped with a steel spring clip, as shown in the accompanying drawing. Test samples were returned to the 100% humidity chamber and stored for the specified period before measuring adhesive strengths. Adhesive strength was measured as "peel strength"—the force required to pull the strip apart when the two ends of the strip were pulled apart in a straight line at a constant rate (1 ft/min).

The results of adhesive testing of the monomer, bis-(4-isocyanatobenzoyl)-tetraethylene glycol, with a variety of catalysts are summarized in Table 1. The values quoted are the averages of 2–5 determinations in each case.

EXAMPLE 3

Testing of Adhesives Using a Rat Skin Model

Tissue specimens were obtained by excising samples (approx. 4×4 inch) from the dorsal region of previously shaved rats. Samples were rinsed to remove animal hair, sealed in plastic bags and sterilized by $^{60}$cobalt irradiation. Immediately prior to use, the specimens were cut into strips (1 inch×½ inch).

Adhesive samples were prepared by thoroughly mixing the components in the specified ratio. A thin film of the mixture was applied to a 1 sq. cm. area on one strip of skin, and a second strip laid over the top to provide an area of overlap of ½ inch containing the adhesive. The strips were clamped under a constant load for the specified time before measuring tensile strengths using an Instron. The results of these studies using a variety of catalysts are summarized in Table 2.

TABLE 1

Adhesive Strengths of Bis-(4-Isocyanatobenzoyl)-Tetraethylene Glycol-Derived Adhesives as a Function of Catalysts Used

| Catalyst | Catalyst/NCO (mole/mole) | Adhesive Strength (g/0.5 inch)[a] | | | |
|---|---|---|---|---|---|
| | | 1 min. | 2 min. | 5 min. | 60 min. |
| 2,3,5-Trimethyl-pyrazine | 0.05 | — | — | 166 | 208 |
| 2,3,5-Trimethyl-pyrazine | 0.50 | — | 30 | 96 | 78 |
| 1,2,4-Trimethyl-piperazine | 0.05 | — | — | 75 | 178 |
| 1,2,4-Trimethyl-piperazine | 0.15 | — | 103 | 196 | 364 |
| 1,2,4-Trimethyl-piperazine | 0.50[b] | — | 23 | — | 37 |
| 4-(N,N—Dimethylamino)-pyridine[c] | 0.01 | — | 5 | 146 | 300 |
| 4-(N,N—Dimethylamino)-pyridine[c] | 0.05 | — | 5 | 94 | 210 |
| 4-(N,N—Dimethylamino)-pyridine[c] | 0.10 | — | 20 | 56 | 126 |
| 4-(N,N—Dimethylamino)-pyridine[d] | 0.02[e] | — | 30 | 168 | 338 |
| 4-(N,N—Dimethylamino)-pyridine[d] | 0.10[b] | — | 35 | 43 | 83 |
| N—Methylmorpholine | 0.10 | — | 5 | 100 | 118 |
| N—Methylmorpholine | 0.20 | — | 105 | 184 | 306 |
| N—Methylmorpholine | 0.30 | — | 75 | 108 | 196 |
| N—(N,N—Dimethylamino-propyl)-2-pyrrolidone | 0.10 | — | — | 104 | 254 |
| N—(N,N—Dimethylamino-propyl)-2-pyrrolidone | 0.20[e] | — | 125 | 152 | 186 |
| 2,4,6-Collidine | 0.10 | — | 75 | 166 | 238 |
| 2,4,6-Collidine | 0.20[e] | — | 85 | 144 | 220 |
| 4-t-Butylpyridine | 0.10 | — | 15 | 220 | 320 |
| 4-t-Butylpyridine | 0.20[e] | — | 190 | 60 | 106 |
| Pyrimidine | 0.20 | — | 23 | 126 | 140 |
| Pyrimidine | 0.30 | — | 25 | 140 | 76 |
| Pyrimidine | 0.60 | — | 67 | 125 | 55 |
| Quinaldine | 0.20 | — | 90 | 246 | 324 |
| Quinaldine | 0.30[f] | — | 105 | 90 | 124 |
| Triethanolamine | 0.15 | — | 27 | 85 | 173 |
| Triethanolamine | 0.30 | — | 64 | — | 122 |
| 3-Pyridyl Carbinol | 0.05 | — | 5 | 64 | 46 |
| 3-Pyridyl Carbinol | 0.10 | — | 5 | 90 | 56 |
| 3-Pyridyl Carbinol | 0.20[b] | — | 50 | 23 | 20 |
| Di-t-Butyl Tin Dilaurate | 0.05 | — | 5 | 124 | 208 |
| Di-t-Butyl Tin Dilaurate | 0.15 | — | 8 | 74 | 169 |
| Di-t-Butyl Tin Dilaurate | 0.30 | — | 3 | 43 | 202 |
| Stannous 2-Ethyl Hexanoate | 0.05 | — | 3 | 89 | 303 |
| Stannous 2-Ethyl Hexanoate | 0.15 | — | 5 | 70 | 328 |
| Tris-(Dimethylamino-methyl)-phenol | 0.015 | — | — | 24 | 268 |
| Tris-(Dimethylamino-methyl)-phenol | 0.03 | — | — | 23 | 67 |
| Tris-(Dimethylamino-methyl)-phenol | 0.10 | — | 40 | 15 | 30 |
| Tetramethyldiamino-2-propanol | 0.03 | — | — | — | 105[g] |
| Tetramethyldiamino-2-propanol | 0.125 | — | — | — | 5[g] |
| Tetramethyldiamino-2-propanol | 0.25 | — | 34 | — | — |
| Pyridine | 0.05 | — | — | 95 | 342 |
| " | 0.50 | 323 | 438 | — | >500 |

TABLE 1-continued

Adhesive Strengths of Bis-(4-Isocyanatobenzoyl)-Tetraethylene Glycol-Derived Adhesives as a Function of Catalysts Used

| Catalyst | Catalyst/NCO (mole/mole) | Adhesive Strength (g/0.5 inch)[a] 1 min. | 2 min. | 5 min. | 60 min. |
|---|---|---|---|---|---|
| Triethanolamine/1,2,4-Trimethylpiperazine[h] | — | 107 | 129 | — | 388 |
| Triethylamine | 0.20 | 185 | 230 | — | — |
| Methyl Nicotinate | 0.40 | 43 | 248 | — | 255 |
| " | 0.50 | 60 | 233 | — | 209 |
| " | 0.60 | 84 | 238 | — | 405 |
| " | 0.80 | 106 | 215 | — | 291 |
| Ethyl nicotinate | 0.30 | 63 | 315 | — | 305 |
| " | 0.50 | 155 | 445 | — | 395 |
| " | 0.70 | 175 | 363 | — | 333 |
| Ethyl 3-pyridyl-acetate | 0.25 | 158 | 460 | — | 495 |
| Ethyl 3-pyridyl-acetate | 0.375 | 305 | 495 | — | >500 |
| Ethyl 3-pyridyl-acetate | 0.50 | 270 | 490 | — | >500 |
| Pyridazine | 0.50 | 11 | 223 | — | 498 |
| " | 1.0 | 64 | 478 | — | >500 |
| " | 1.5 | 140 | 403 | — | 408 |
| " | 2.0 | 183 | 385 | — | 433 |
| Methyl 2-pyrazine carboxylate | 0.1 | — | 25 | 290 | — |
| Methyl 2-pyrazine carboxylate | 0.5 | — | 50 | 345 | — |
| Ethyl 1-Methyl-nipecotate | 0.05 | 70 | 350 | — | — |
| Ethyl 1-Methyl-nipecotate | 0.075 | 198 | 240 | — | — |
| Ethyl 1-Methyl-nipecotate | 0.10 | 90 | 275 | — | — |
| 2-Dimethylamino-ethanol | 0.05 | 102 | 213 | — | — |
| 2-Dimethylamino-ethanol | 0.075 | 185 | 110 | — | — |
| 2-Dimethylamino-ethanol | 0.085 | 195 | 220 | — | — |

[a]Measured using hydrated cellulose as substrate; each value represents the average of 2–5 measurements.
[b]pot-life = 5–10 minutes.
[c]Catalyst dissolved in dimethylformamide.
[d]Catalyst dissolved in dimethylsulfoxide.
[e]Pot-life = 10–20 minutes.
[f]Pot-life = 20–30 minutes.
[g]Measurements made at 15 minutes.
[h]Triethanolamine:1,2,4-trimethylpiperazine:isocyanate = 0.05:0.20:1.0 (molar).

TABLE 2

Adhesive Strengths of Bis-(4-Isocyanatobenzoyl)-Tetraethylene Glycol-Derived Adhesives Using Rat Skin as Substrate

| Catalyst | Catalyst/NCO (mole/mole) | Adhesive Strength (¼ sq. inch) 1 min. | 3 min. | 5 min. |
|---|---|---|---|---|
| Pyridine | 0.50 | 35 | 320 | 290 |
| Ethyl Nicotinate | 0.20 | — | 190 | 115 |
| " | 0.40 | — | 280 | 125 |
| " | 0.60 | — | 250 | 220 |
| " | 0.80 | — | 185 | 200 |
| Ethyl 3-Pyridyl-acetate | 0.20 | 60 | 155 | 180 |
| Ethyl 3-Pyridyl-acetate | 0.40 | 135 | 225 | 220 |
| Ethyl 3-Pyridyl-acetate | 0.60 | 140 | 230 | 155 |
| Ethyl 3-Pyridyl-acetate | 0.80 | 115 | 125 | 185 |
| Triethylamine/Dibutyl-tindiacetate (1:1) | 0.02 | 260 | 320 | — |
| 1,4-Diazabicyclo-(2,2,2)-octane | 0.10 | — | 165 | — |
| Hexamethylenetetramine | 0.10 | — | 130 | — |
| Triethylamine | 0.10 | 120 | 360 | — |
| Triethylamine + N,N—diethylacetamide[b] | 0.10 | 180 | 840 | — |
| Triethylamine + N,N—diethylacetamide[c] | 0.10 | 310 | 840 | — |

[a]Measured using rat skin as substrate (see Example 3).
[b]Isocyanate and catalyst were mixed in the indicated ratio; one drop of this formulation was mixed with one drop of N,N—diethylacetamide and the adhesive mixture applied to the substrate.
[c]The tissue was pretreated with 8% aqueous sodium bicarbonate before applying the adhesive.

EXAMPLE 4

Bis-(4-Isocyanatobenzoyl)-Polyethylene Glycol (M.W.=400)

A. Polyethylene glycol 400 (100 g, 0.25 mole) was treated with p-nitrobenzoyl chloride (113 g, 0.6 mole), following the procedure described in Example 1, Part A. The residual, thick oil was treated with aqueous sodium bicarbonate, as described, to remove excess acid chloride. The product, bis-(4-nitrobenzoyl)-polyethylene glycol 400 (148.3 g) was obtained as a thick, yellow oil.

B. Bis-(4-nitrobenzoyl)-polyethylene glycol 400 (130 g), prepared in Part A, was hydrogenated over palladium on carbon (10%, 7 g), as described in Example 1, Part B, to give bis-(4-aminobenzoyl)-polyethylene glycol 400 (115 g) as a thick, pale yellow oil.

C. Bis-(4-aminobenzoyl)-polyethylene glycol 400 (100 g, from Part B) was phosgenated by the procedure described in Example 1, Part C, to give bis-(4-isocyanatobenzoyl)-polyethylene glycol 400 in quantitative yield, as a thick, pale yellow oil.

D. Adhesive Testing: The monomer was mixed with ethyl 3-pyridylacetate (molar ratio of catalyst to isocyanate=0.1). The mixture was tested using hydrated cellulose as substrate, as described in Example 2, resulting in an adhesive strength of 113 g m./0.5 inch at 2 minutes.

EXAMPLE 5

Bis-(4-Isocyanatobenzoyl)-Polyethylene Glycol (M.W.=600)

A. Following the procedure described in Example 1, Part A, polyethylene glycol 600 (150 g, 0.25 mole) was treated with p-nitrobenzoyl chloride (113 g, 0.6 mole) to give bis-(4-nitrobenzoyl)-polyethylene glycol 600 (208 g) as a thick, yellow oil.

B. Bis-(4-nitrobenzoyl)-polyethylene glycol 600 (120 g), from Part A, was hydrogenated in the usual manner to give bis-(4-aminobenzoyl)-polyethylene glycol 600 (115 g) as a pale yellow oil.

C. The product from Part B (50 g) was phosgenated by the procedure described in Example 1, Part C, to give bis-(4-isocyanatobenzoyl)-polyethylene glycol 600 in quantitative yield, as a thick, pale yellow oil.

D. Adhesive Testing: The monomer was mixed thoroughly with ethyl 3-pyridyl acetate (molar ratio of catalyst to isocyanate=0.2). The resulting adhesive was tested as described in Example 2; adhesive strength=38 gm/0.5 inch at 2 minutes.

EXAMPLE 6

Bis-(4-Isocyanatobenzoyl)-Triethylene Glycol

A. Triethylene glycol (45 g, 0.3 mole) was treated with excess p-nitrobenzoyl chloride (116 g, 0.62 mole), following the general procedure outlined in Example 1, Part A. After treating with aqueous sodium bicarbonate to remove excess acid chloride, the product was recrystallized from ethyl acetate to give bis-(4-nitrobenzoyl)-triethylene glycol (115 g) as a pale yellow solid, m.p. 104°–105° C. The product was homogeneous by TLC.

B. Bis-(4-nitrobenzyoyl)-triethylene glycol (50 g) was hydrogenated in the usual manner over palladium on carbon (10%, 3 g). The product was recrystallized from ethyl acetate in the dark to give bis-(4-aminobenzoyl)-triethylene glycol (42 g) as a white solid, which was homogeneous by TLC.

C. Bis-(4-aminobenzoyl)-triethylene glycol (25 g), from Part B, was phosgenated by the procedure described in Example 1, Part C, to give bis-(4-isocyanatobenzoyl)-triethylene glycol in quantitative yield as a pale yellow solid, m.p. 64.2°–65.1° C.

D. Adhesive Testing: The isocyanate monomer, prepared as described in Part A, was mixed in equimolar proportions with bis-(4-isocyanatobenzoyl)-tetraethylene glycol (from Example 1) and the mixture warmed gently to produce a homogeneous mixture. On cooling, ethyl 3-pyridylacetate was mixed thoroughly with the mixture (molar ratio of catalyst to isocyanate=0.25) and the adhesive tested using hydrated cellulose as substrate, as described in Example 2. Adhesive strength=483 gm/0.5 inch at 2 minutes.

EXAMPLE 7

Bis-(4-Isocyanatobenzoyl)-Diethylene Glycol

A. Diethylene glycol (31.8 g, 0.3 mole) and p-nitrobenzoyl chloride (116 g, 0.62 mole) were reacted under the conditions described in Example 1, Part A. The product was crystallized from ethyl acetate to give bis-(4-nitrobenzoyl)-diethylene glycol (101 g) as a pale yellow solid, m.p. 100°–102° C. The product was homogeneous by TLC.

B. The product from Part A (90 g, 0.25 mole) was hydrogenated in the usual manner over palladium on carbon (10%, 5 g). The product was crystallized from ethyl acetate, in the dark, to give bis-(4-aminobenzoyl)-diethylene glycol (62 g) as a white solid, m.p. 101°–104° C. which was homogeneous by TLC.

C. The product from Part B (25 g) was phosgenated as described in Example 1, Part C, to give bis-(4-isocyanatobenzoyl)-diethylene glycol in quantitative yield as a pale yellow solid, m.p. 45°–48° C.

D. Adhesive Testing: The isocyanate monomer was melted by warming gently and ethyl 3-pyridylacetate mixed thoroughly with the monomer (molar ratio of catalyst to isocyanate=0.4). The resulting adhesive mixture was tested as described in Example 2, to give an adhesive strength of 118 gm/0.5 inch at 2 minutes.

Alternatively, the monomer, prepared as described in Part C, was mixed in equimolar proportions with bis-(4-isocyanatobenzoyl)-tetraethylene glycol, with gentle warming if necessary to achieve homogeneity. Ethyl 3-pyridylacetate was mixed thoroughly with the adhesive mixture (molar ratio of catalyst to isocyanate=0.5). The mixture was tested as described in Example 2 to give an adhesive strength of >500 gm/0.5 inch at 2 minutes.

EXAMPLE 8

Bis-(4-Isocyanatobenzoyl)-Propane-1,3-Diol

A. Bis-(4-aminobenzoyl)-propane-1,3-diol (3.14 g, 0.01 mole) was phosgenated as described in Example 1, Part C, to give bis-(4-isocyanatobenzoyl)-propane-1,3-diol (3.2 g) as a pale yellow solid, m.p. 97°–102° C.

B. Adhesive Testing: The isocyanate monomer, prepared as described in Part A, was mixed in a molar ratio of 1:9 with bis-(4-isocyanatobenzoyl)-tetraethylene glycol with gentle warming to achieve homogeneity. On cooling, ethyl 3-pyridylacetate was mixed thoroughly with the adhesive mixture (molar ratio of catalyst to isocyanate=0.5) and the mixture tested as described in Example 2. Adhesive strength=498 gm/0.5 inch at 2 minutes.

EXAMPLE 9

Bis-(3-Isocyanatobenzoyl)-Tetraethylene Glycol

A. Tetraethylene glycol (58.2 g, 0.3 mole) was treated with m-nitrobenzoyl chloride, following the general procedure described in Example 1, Part A. After the usual work-up, the product was crystallized from ethyl acetate/hexanes at −20° C. for 3 days to give bis-(3-nitrobenzoyl)-tetraethylene glycol (110 g) as a pale yellow solid, m.p. 38°–40° C.

B. Bis-(3-nitrobenzoyl)-tetraethylene glycol (100 g, from Part A) was hydrogenated over palladium on carbon (10%, 6 g), following the usual procedure.

When hydrogen uptake was complete (27.95 liters total) the mixture was stirred for two hours at room temperature under hydrogen. After removal of the hydrogen in vacuo, magnesium sulfate was added directly to the mixture which was stirred for a further 2 hours at room temperature and then filtered. The product was precipitated directly as an oil by addition of hexanes to the filtrate. The supernatent was decanted, the residue redissolved in isopropanol and excess hydrogen chloride/dioxane (4N) added. The hydrochloride salt of the desired product crystallized at −20° C. and was recrystallized from isopropanol/tetrahydrofuran to give bis-(3-aminobenzoyl)-tetraethylene glycol dihydrochloride (75 g) as a pale yellow solid, m.p. 100°–101.5° C. The product was homogeneous by TLC.

C. The product from Part B (25 g) was phosgenated in the usual manner, as described in Example 1, Part C, to give bis-(3-isocyanatobenzoyl)-tetraethylene glycol in quantitative yield as a thick yellow oil. The product solidified on prolonged storage at −15° C.; m.p. 36°–39° C.

D. Adhesive Testing: The isocyanate monomer, prepared as described in Part C, was mixed thoroughly with ethyl 3-pyridylacetate (molar ratio of catalyst to isocyanate=0.4). The adhesive mixture was tested as described in Example 2, using hydrated cellulose as substrate. Adhesive strength=450 gm/0.5 inch at 2 minutes.

EXAMPLE 10

Bis-(2-Isocyanatobenzoyl)-Tetraethylene Glycol

A. Tetraethylene glycol (58.2 g, 0.3 mole) was treated with o-nitrobenzoyl chloride (116 g, 0.625 mole), under the general conditions described in Example 1, Part A. Following the usual work-up procedure, bis-(2-nitrobenzoyl)-tetraethylene glycol (124 g) was obtained as a yellow oil which was homogeneous by TLC.

B. The product from Part A (32 g, 0.07 mole) was dissolved in redistilled ethyl acetate (200 ml) and hydrogenated over palladium on carbon (10%, 1.5 g) using a Parr hydrogenation apparatus at 50 p.s.i. When hydrogen uptake was complete (4 days), magnesium sulfate was added directly to the mixture, which was stirred at room temperature for 2 hours. After filtration, the filtrate was evaporated to dryness, redissolved in methanol and treated with excess anhydrous hydrogen chloride/dioxane (4N). The mixture was diluted with two volumes of tetrahydrofuran and evaporated to dryness. The solid residue was recrystallized from methanol/tetrahydrofuran to give bis-(2-aminobenzoyl)-tetraethylene glycol (23 g) as a white solid, m.p. 98°–102° C., which was homogeneous by TLC.

C. The product from Part B (5.1 g, 0.01 mole) was phosgenated in the usual manner to give bis-(2-isocyanatobenzoyl)-tetraethylene glycol (4.1 g) as a light brown oil.

D. Adhesive Testing: The isocyanate monomer, prepared as described in Part C, was warmed gently to give a melt which was mixed thoroughly with ethyl 3-pyridylacetate (molar ratio of catalyst to isocyanate=0.4) and the adhesive mixture tested as described in Example 2. Adhesive strength=0 gm/0.5 inch at 2 minutes.

EXAMPLE 11

Bis-(4-Isocyanatobenzenesulfonyl)-Tetraethylene Glycol

A. p-Nitrobenzenesulfonyl chloride (25 g, 0.113 mole) and tetraethylene glycol (10 g, 0.052 mole) was dissolved in dry tetrahydrofuran and treated with triethylamine (15 ml, 0.110 mole). The mixture was stirred overnight at room temperature when TLC revealed that reaction was incomplete. Further portions of acid chloride (12 g) and triethylamine (7 ml) were therefore added and the mixture stirred for a further 4 hours at room temperature. An equal volume of saturated aqueous sodium bicarbonate was then added, the mixture stirred at room temperature for 4 hours and then extracted with ethyl acetate (2×). The combined organic extracts were washed with saturated sodium chloride (4×), dried (MgSO4) and evaporated under reduced pressure. The residue was crystallized from ethyl acetate/hexanes to give bis-(4-nitrobenzenesulfonyl)-tetraethylene glycol (15.5 g) as a pale yellow solid, m.p. 59°–62° C., which was homogeneous by TLC.

B. Bis-(4-nitrobenzenesulfonyl)-tetraethylene glycol (10 g, from Part A) was dissolved in distilled ethyl acetate (200 ml) and hydrogenated over palladium on carbon (10%, 0.5 g) at 40 p.s.i. in a Parr hydrogenation apparatus. The solution was filtered and evaporated under reduced pressure to give bis-(4-aminobenzenesulfonyl)-tetraethylene glycol in quantitative yield as a thick, yellow oil which was homogeneous by TLC.

C. The product from Part B (8 g) was phosgenated in the usual manner to give bis-(4-isocyanatobenzenesulfonyl)-tetraethylene glycol (8.3 g) as a thick yellow oil.

D. Adhesive Testing: The isocyanate monomer, prepared as described in Part C, was mixed thoroughly with triethylamine (molar ratio of catalyst to isocyanate=0.2) and the adhesive mixture tested as described in Example 2, using hydrated cellulose as substrate. Adhesive strength=50 gm/0.5 inch at 10 minutes.

EXAMPLE 12

Bis-(4-Isocyanatobenzoyl)-Dipropylene Glycol

A. Dipropylene glycol (40.2 g, 0.3 mole) was treated with p-nitrobenzoyl chloride (116 g, 0.625 mole), following the general procedure described in Example 1, Part A. After treatment with saturated aqueous sodium bicarbonate in the usual manner, the ethyl acetate solution of the product was dried (MgSO4), filtered and crystallization effected by the addition of hexanes. The product, bis-(4-nitrobenzoyl)-dipropylene glycol (67 g), was isolated as a pale yellow solid, m.p. 96°–100° C. which was homogeneous by TLC.

B. Bis-(4-nitrobenzoyl)-dipropylene glycol (50 g, 0.134 mole, from Part A) was hydrogenated in the usual manner over palladium on carbon (10%, 4 g). The product crystallized during drying over MgSO4. The solution was therefore heated to boiling, filtered hot and crystallization effected by addition of hexanes to give bis-(4-aminobenzoyl)-dipropylene glycol (29 g) as an offwhite solid, m.p. 163°–165° C. which was homogeneous by TLC.

C. The product from Part B (3.72 g, 0.01 mole) was phosgenated in the usual manner to give bis-(4-isocyanatobenzoyl)-dipropylene glycol (3.69 g) as a pale yellow solid, m.p. 90°–100° C.

D. Adhesive Testing: The isocyanate monomer, prepared as described in Part C, was mixed in a molar ratio of 1:3 with bis-(4-isocyanatobenzoyl)-tetraethylene glycol (Example 1) with gentle warming to achieve homogeneity. On cooling, ethyl 3-pyridylacetate was mixed thoroughly with the adhesive mixture (molar ratio of catalyst to isocyanate=0.5) and the adhesive tested as described in Example 2. Adhesive strength=>500 gm/0.5 inch at 2 minutes.

EXAMPLE 13

Bis-(4-Isocyanatobenzoyl)-Tripropylene Glycol

A. Tripropylene glycol (57.6 g, 0.3 mole) was treated with p-nitrobenzoyl chloride (116 g, 0.625 mole), following the general procedure described in Example 1, Part A. The product, bis-(4-nitrobenzoyl)-tripropylene glycol (131 g), was obtained as a viscous yellow oil.

B. Bis-(4-nitrobenzoyl)-tripropylene glycol (120 g, 0.28 mole, from Part A) was hydrogenated in the usual manner over palladium on carbon (10%, 5 g). When hydrogen uptake was complete, magnesium sulfate was added directly to the mixture which was stirred at room temperature for several hours, filtered and evaporated to dryness under reduced pressure. The residue was redissolved in a minimum volume of isopropanol and the product converted to the dihydrochloride salt by addition of excess, anhydrous hydrogen chloride in dioxane. Crystallization was effected by addition of tetrahydrofuran to the solution, to give bis-(4-aminobenzoyl)tripropylene glycol dihydrochloride (67 g) as a white solid, m.p. 189°-193° C., which was homogeneous by TLC.

C. The product from Part B (2.5 g, 0.005 mole) was phosgenated in the usual manner to give bis-(4-isocyanatobenzoyl)-tripropylene glycol in quantitative yield as a very viscous, yellow oil.

D. Adhesive Testing: The isocyanate monomer, prepared as described in Part C, was mixed thoroughly with ethyl 3-pyridylacetate (molar ratio of catalyst to isocyanate=0.4) and the adhesive tested as described in Example 2, to give and adhesive strength of 105 gm/0.5 inch at 2 minutes.

Alternatively, the adhesive monomer, prepared as described in Part C, was mixed in equimolar proportions with bis-(4-isocyanatobenzoyl)-tetraethylene glycol (from Example 1). Ethyl 3-pyridylacetate was mixed thoroughly with the mixture of monomers (molar ratio of catalyst to isocyanate=0.3) and the adhesive was tested as described in Example 2. Adhesive strength=475 gm/0.5 inch at 2 minutes.

EXAMPLE 14

Tris-(4-Isocyanatobenzoyl)-Trimethylolpropane

A. Trimethylolpropane (26.84 g, 0.2 mole) was treated with p-nitrobenzoyl chloride (117 g, 0.63 mole), following the general procedure described in Example 1. Part A. The product was worked up in the usual way, except that precipitation occurred during the treatment with saturated aqueous sodium bicarbonate. The mixture was therefore heated to effect solution, the phases separated, the organic phase washed with saturated sodium bicarbonate (3×), and dried over MgSO$_4$. The product crystallized during drying and the mixture was therefore heated to boiling, filtered hot, the solid washed with hot ethyl acetate and hexanes added to the filtrate to induce crystallization. The product, tris-(4-nitrobenzoyl)-trimethylolpropane (67 g) was obtained at a pale yellow solid, m.p. 104°-106° C., which was homogeneous by TLC.

B. The product from Part A (15 g, 0.026 mole) was slurried in distilled ethyl acetate (200 ml) and hydrogenated over palladium on carbon (10%, 1 g) in a Parr hydrogenation apparatus at 50 p.s.i. When hydrogen uptake was complete (20 hours), the solution was filtered and the filtrate dried (MgSO$_4$). The product crystallized during drying and the mixture was therefore heated to boiling, filtered hot and the solid washed with hot ethyl acetate and hot tetrahydrofuran. The combined filtrates were evaporated to dryness under reduced pressure and the residue triturated with ethyl acetate/tetrahydrofuran. After standing overnight at −15° C., the solid was filtered to give tris-(4-aminobenzoyl)-trimethylolpropane (9 g) as a white solid, m.p. 210°-212° C., which was homogeneous by TLC.

C. The product from Part B (2.5 g, 0.005 mole) was phosgenated in the usual manner to give tris-(4-isocyanatobenzoyl)-trimethylolpropane in quantitative yield as a viscous, yellow oil.

D. Adhesive Testing: The isocyanate monomer, prepared as described in Part C, was mixed thoroughly with ethyl 3-pyridylacetate (molar ratio of catalyst to isocyanate=0.2) and the adhesive tested as described in Example 2. Adhesive strength=93 gm/0.5 inch at 1 minute.

EXAMPLE 15

Bis-(4-Isocyanatobenzoyl)-Dihydroxyethyladipate

A. A mixture of p-nitrobenzoic acid (33.4 g, 0.2 mole), ethylene carbonate (19.4 g, 0.22 mole) and tetraethylammonium iodide (9.6 g, 0.036 mole) was heated at 140° C. for 45 minutes. On cooling, the mixture was dissolved in ethyl acetate (500 ml) and washed with water (3×) and saturated sodium chloride. The organic solution was dried (MgSO$_4$) and evaporated to dryness under reduced pressure. The residue was shown to be a mixture of the desired product and a small amount of the diester product, bis-(4-nitrobenzoyl)-ethylene glycol, by TLC (silica gel, ethyl acetate as mobile phase; R$_f$'s=0.5 and 0.7, respectively). The mixture was therefore chromatographed on silica gel, eluting first with benzene and then with chloroform to give hydroxyethyl p-nitrobenzoate (31 g) as a pale yellow solid, m.p. 77°-78° C., which was homogeneous by TLC.

B. A solution of hydroxyethyl p-nitrobenzoate (29.5 g, 0.14 mole) in tetrahydrofuran (150 ml) was cooled to 0° C. and treated with a solution of adipoyl chloride (12.4 g, 0.068 mole) in tetrahydrofuran (50 ml), followed by pyridine (12.9 g, 0.160 mole). The mixture was allowed to warm to room temperature slowly and stirred overnight. The solid pyridine hydrochloride was then removed by filtration, and the filtrate evaporated under reduced pressure to half the volume. The solution was then diluted with a little methanol, heated to reflux and filtered while hot. The product, bis-(4-nitrobenzoyl)-dihydroxyethyladipate (33 g) crystallized on standing as a pale yellow solid, m.p. 100°-101° C., which was homogeneous by TLC.

C. The product from Part B (10.0 g) was hydrogenated in the usual manner over palladium on carbon (10%, 1 g) in a Parr hydrogenation apparatus at 50 p.s.i. When hydrogenation was complete (20 hours) magnesium sulfate was added directly to the mixture which was stirred at room temperature for several hours. The mixture was then filtered directly into the phosgenation apparatus under nitrogen. The solvent was evaporated under a stream of nitrogen, the residue redissolved in dry dioxane and phosgenated in the usual manner to give bis-(4-isocyanatobenzoyl)-dihydroxyethyladipate in quantitative yield as a pale yellow solid, m.p. 92°–96° C.

D. Adhesive Testing: The isocyanate monomer, prepared as described in Part C, was mixed in a molar ratio of 1:3 with bis-(4-isocyanatobenzoyl)-tetraethylene glycol (Example 1), with gentle warming to achieve homogeneity. On cooling, ethyl 3-pyridylacetate was mixed thoroughly with the adhesive mixture (molar ratio of catalyst to isocyanate=0.25) and the adhesive tested as described in Example 2. Adhesive strength=475 gm/0.5 inch at 2 minutes.

EXAMPLE 16

Bis-(2,4-Diisocyanatobenzoyl)-Tetraethylene Glycol

A. 2,4-Dinitrobenzoic acid (25 g, 0.11 mole) was suspended in dry dichloromethane (100 ml), the mixture cooled to 0° C. and treated dropwise with a solution of carbonyl diimidazole (20.6 g, 0.125 mole) in dry dichloromethane (150 ml) over 25 minutes. The mixture was stirred at 0° C. for a further 30 minutes before adding a solution of tetraethylene glycol (9.7 g, 0.05 mole) in dry dichloromethane (100 ml) dropwise over 20 minutes. The mixture was allowed to warm to room temperature slowly, stirred at this temperature for 6 days and then evaporated to dryness under reduced pressure. The residue was redissolved in ethyl acetate and washed with 2N hydrochloric acid (3×), saturated sodium bicarbonate (3×), water and dried (mgSo4). Evaporation of the solvent gave the product bis-(2,4-dinitrobenzoyl)-tetraethylene glycol (17.2 g) as a viscous yellow oil which was homogeneous by TLC.

B. The product from Part A (10 g) was hydrogenated in the usual manner over palladium on carbon (10%, 1 g) in a Parr hydrogenation apparatus at 50 p.s.i. When hydrogen uptake was complete (20 hours) magnesium sulfate was added directly to the mixture which was stirred for several hours at room temperature, then filtered and evaporated to dryness under reduced pressure. The residue was redissolved in a minimum volume of isopropanol and converted to the tetrahydrochloride salt by treatment with excess, anhydrous hydrogen chloride in dioxane. Crystallization was effected by addition of tetrahydrofuran to the solution to give bis-(2,4-diaminobenzoyl)-tetraethylene glycol tetrahydrochloride (7.4 g) as an off-white solid, which was homogeneous by TLC.

C. The product from Part B (5 g) was phosgenated in the usual manner to give bis-(2,4-diisocyanatobenzoyl)-tetraethylene glycol in quantitative yield as a viscous, yellow oil.

D. Adhesive Testing: The isocyanate monomer, prepared as described in Part C, was mixed thoroughly with ethyl 3-pyridylacetate (molar ratio of catalyst to isocyanate=0.5) and the adhesive tested as described in Example 2. Adhesive strength=∼30 gm/0.5 inch at 2 minutes.

EXAMPLE 17

Bis-(3-Isocyanatopropionyl)-Tetraethylene Glycol

A. N-t-Butyloxycarbonyl-β-alanine (75.6 g, 0.4 mole) was coupled with tetraethylene glycol (36.9 g, 0.19 mole), using carbonyl diimidazole (72.6 g, 0.44 mole), following the general procedure described in Example 16, Part A. When reaction was complete, the reaction mixture was evaporated to dryness under reduced pressure. The residue was redissolved in ethyl acetate and washed with 2N hydrochloric acid (3×), saturated sodium bicarbonate (3×), water and dried (MgSO4). The mixture was filtered and the filtrate evaporated under reduced pressure to give bis-(t-butyloxycarbonyl-β-alanyl)-tetraethylene glycol (93 g) as a syrup which failed to crystallize. The product was shown to contain a trace of t-butyloxycarbonyl-β-alanine by TLC.

B. The product from Part A (93 g) was treated with anhydrous hydrogen chloride in dioxane (4N, 200 ml) for 1 hour at room temperature. The mixture was evaporated to dryness under reduced pressure and the residue crystallized from isopropanol/tetrahydrofuran to give bis-(β-alanyl)-tetraethylene glycol dihydrochloride as a white amorphous solid which was homogeneous by TLC.

C. The product from Part B (10 g) was phosgenated in the usual manner to give bis-(3-isocyanatopropionyl)-tetraethylene glycol in quantitative yield as a viscous oil.

D. Adhesive Testing: The isocyanate monomer, prepared as described in Part C, was mixed thoroughly with ethyl 3-pyridylacetate (molar ratio of catalyst to isocyanate=0.5) and the adhesive tested as described in Example 2. Adhesive strength=∼10 gm/0.5 inch at 2 minutes.

EXAMPLE 18

Bis-(4-Isothiocyanatobenzoyl)-Tetraethylene Glycol

A. Bis-(4-aminobenzoyl)-tetraethylene glycol (10 g, 0.023 mole), prepared as described in Example 1, Part B, was dissolved in dry dioxane and thiophosgenated, following the general procedure described in Example 1, Part C, using thiophosgene (85% in carbon tetrachloride, 11.5 ml, 0.125 mole) in place of phosgene. After work-up, the product, bis-(4-isothiocyanatobenzoyl)-tetraethylene glycol, was obtained in quantitative yield as a brown oil.

B. Adhesive Testing: The isothiocyanate monomer, prepared as described in Part A, was mixed thoroughly with pyridine (molar ratio of catalyst to isothiocyanate=0.5) and the adhesive tested as described in Example 2. Adhesive strength=0 gm/0.5 inch at 2 minutes.

EXAMPLE 19

Effect of Curing Agents on Adhesive Strength

The isocyanate monomer, bis-(4-isocyanatobenzoyl)-tetraethylene glycol, prepared as described in Example 1, was mixed thoroughly in various proportions with curing agents, such as glycerol or diethylene glycol. The catalyst, ethyl 3-pyridylacetate was added (molar ratio of catalyst to isocyanate=0.4), mixed thoroughly and the adhesives tested using hydrated cellulose as substrate, as described in Example 2. The results of these studies are summarized in Table 3.

TABLE 3

| | Effect of Curing Agents | | |
|---|---|---|---|
| | | Adhesive Strength (g/0.5 inch)[b] | |
| Curing Agent | C.A./NCO[a] (mole/mole) | 1 min. | 2 min. |
| Glycerol | 0.05 | 483 | 500 |
| " | 0.10 | 500 | 500 |
| Diethylene Glycol | 0.05 | 350 | 470 |
| " | 0.10 | 408 | 500 |

TABLE 3-continued

Effect of Curing Agents

| Curing Agent | C.A./NCO[a] (mole/mole) | Adhesive Strength (g/0.5 inch)[b] | |
|---|---|---|---|
| | | 1 min. | 2 min. |
| " | 0.15 | 330 | 493 |
| None | — | 495 | 470 |

[a]Molar ratio of curing agent (C.A.) to isocyanate.
[b]Measured using hydrated cellulose as substrate, as described in Example 2.

EXAMPLE 20

Bis(4-isocyanatobenzoyl-polyglycolyl)-diethylene glycol

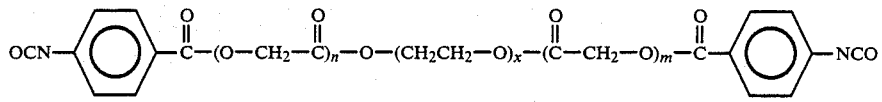

Where $n + m \approx 4$ and $x = 2$

A. Diethylene glycol (16 g., 0.151 mole), Glycolide (glycolic acid cyclic dimer) (34 g., 0.2928 mole) and lead oxide (~2 mg.) were placed in a dry 100 ml. 3 neck round bottom flask equipped with an oil bath and magnetic stirrer. The mixture was brought to 140° C. with stirring and this temperature was maintained for about 20 hrs. The cooled reaction was evaluated by NMR and IR spectroscopy, which showed complete conversion to Bis-(polyglycolyl)-diethylene glycol. The Bis-(polyglycolyl)-diethylene glycol was stored under nitrogen and used in the following step without further purification.

B. Bis-(polyglycolyl)-diethylene glycol (50 g., 0.151 mole) from part A above, and 4-dimethylamino pyridine (44.7 g., 0.332 mole) were dissolved in dry, distilled tetrahydrofuran (800 ml.) in a one liter erlenmeyer flask equipped with a magnetic stirrer. 4-Nitrobenzoylchloride (61.7 g., 0.332 mole) dissolved in dry, distilled tetrahydrofuran (200 mls.) was added in two portions to the vigorously stirred solution above. The reaction was complete about five minutes after the second addition (by TLC in methanol/chloroform; 15/85). The off-white solid (dimethylaminopyridine hydrochloride) was removed by filtration and washed with a small volume of tetrahydrofuran. The combined filtrate and wash were concentrated under reduced pressure to about 300 ml. Ethyl acetate (1 liter) was added. The resulting solution was stirred vigorously for about 18 hours with one liter of saturated sodium bicarbonate. The organic phase was separated and washed with 500 ml. of saturated sodium bicarbonate (1×), 500 ml. water (1×), 300 ml. of 1N hydrochloric acid (2×) and 300 ml. of saturated sodium chloride) (2×). The resulting solution was dried by stirring with MgSO4, and the MgSO4 removed by filtration. The product (Bis-(4-nitrobenzoyl-polyglycolyl)-diethylene glycol) was homogeneous by TLC (chloroform/methanol; 85/15; Silica). The solvent was removed from a small aliquot under reduced pressure, and the structure confirmed by NMR and IR spectroscopy. The remaining ethyl acetate solution was used "as is" for the next step.

C. Bis-(4-nitrobenzoyl-polyglycolyl)-diethylene glycol in ethyl acetate (the total solution from part B above) was placed in a 3 liter round bottom flask and 10% palladium on carbon (6 g.) added. The mixture was vigorously agitated under an atmosphere of hydrogen until gas uptake ceased. During the hydrogenation, the temperature was kept below 30° C. by the periodic cooling of the reaction in an ice bath. After hydrogen uptake had stopped, the mixture was agitated an additional two hours at room temperature. The catalyst was removed by filtration (caution! product is light and oxygen sensitive) and the filtrate concentrated in vacuo. The product was lyophilized three times from dry, distilled dioxane and used "as is" in the following step. The structure of the Bis-(4-aminobenzoyl-polyglycolyl)-diethylene glycol was confirmed by NMR spectroscopy and was shown to be homogeneous on TLC (chloroform/methanol; 85/15; silica gel).

D. Bis-(4-aminobenzoyl-polyglycolyl)-diethylene glycol (the total from part C) was dissolved in dry, distilled, deoxygenated dioxane (500 ml.) in a 2 liter, 3 neck round bottom flask equipped with a reflux condenser, drying tube, magnetic stirrer, nitrogen purge, and an oil bath for heating. The solution was purged with nitrogen, and 4N hydrogen chloride in dioxane (30 ml., 0.12 mole) was added while purging continued. Phosgene in dioxane (4M, 60 ml., 0.24 mole) was added to the above stirred slurry via a nitrogen pressure transfer system. The stirred reaction was brought to 80° C. over a period of one to two hours and maintained at this temperature until complete solution occurred. Once a clear solution was obtained, the mixture was heated slowly to reflux and very mild reflux maintained for two hours. The condenser was then rearranged for distillation, and solvent removed by distillation at atmospheric pressure until the volume of the reaction mixture was reduced to approximately one third. The reaction mixture was allowed to cool to room temperature and then lyophilized. Extreme care must be taken during all subsequent manipulation to ensure that no moisture contacts the product. The lyophilized material was heated at 80° C. under high vacuum with magnetic stirring in order to drive off all traces of dioxane. Bis-(4-isocyanatobenzoyl-polyglycolyl)-diethylene glycol was obtained as an extremely viscous amber oil which was stored without deterioration under dry nitrogen at −20° C. for extended periods of time. The structure was confirmed by IR and NMR spectroscopy.

EXAMPLE 21

Testing of Adhesives Using a Rat Skin Model

Two sections of rat skin (obtained as described in Example 3) are placed face to face and cut into 0.5 inch squares. The resulting "sandwiches" are stored at −20° C. until needed.

Adhesive samples were prepared by dissolving the isocyanate monomer (in this case, Bis-(isocyanatobenzoylpolyglycolyl)-diethylene glycol from Example 20) in dichlorofluoromethane (40–45% by weight), cooling to ~ −10° C. and adding triethylamine (60 μl per gram of monomer). The pot life of this solution was about 30 minutes. To obtain the adhesives peel strength, a frozen "sandwich" of rat skin was removed from the freezer and immediately clamped on one edge with a ball clamp. The tissues were pulled apart and the fat was removed from both sides. The tissue was then reclamped on the opposite edge and the rest of the fat removed. The tissues were folded back to the clamp and a few drops of the cold solution prepared above was applied to the interface of the two rat skins. As the solution warmed, the solvent evaporated and the moisture on the tissue started the polymerization. The two tissues were pressed together several times at the point of application, and then the clamp was moved to exert pressure at this point. After one minute, the clamp was removed and the force required to pull the tissues apart This material was prepared exactly as per Example 20, except polyethylene glycol 200 (30.2 g., 0.151 mole) was substituted for diethylene glycol.

Adhesive Testing: The monomer was prepared and tested as described in Example 21. Adhesive strength ≈80 grams/0.5 inch at 1 minute.

EXAMPLE 24

Bis-(4-isocyanatobenzoyl-polyglycolyl)-polyethylene glycol 300

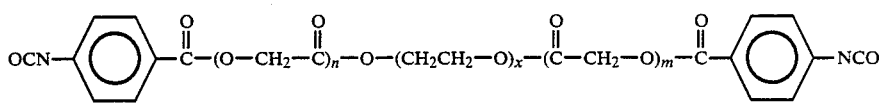

Where n + m ≈ 4 and x ≈ 6 measured (in grams/0.5 inch). The peel strength was obtained by averaging the values of from 2-6 of the above experiments. The peel strength of the monomer from Example 20 was 92 grams/0.5 inch at 1 minute.

EXAMPLE 22

Bis-(4-isocyanatobenzoyl-polyglyolyl)-polyethylene glycol 600

This material was prepared exactly as described in Example 20, except polyethylene glycol 300 (45.3 g., 0.151 mole) was substituted for diethylene glycol.

Adhesive Testing: This monomer was prepared and tested as described in Example 21. Adhesive strength ≈45 grams/0.5 inch at 1 minute.

EXAMPLE 25

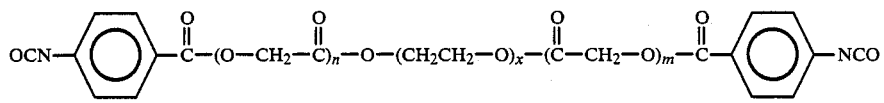

Where n + m ≈ 4 and x ≈ 13

This material was prepared exactly as per Example 20, except polyethylene glycol 600 (90.6 g.; 0.151 mole) was substituted for diethylene glycol.

Bis-(4-isocyanatobenzoyl-polyglycolyl)-polyethylene glycol 400

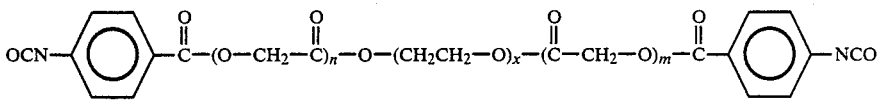

Where n + m ≈ 4 and x ≈ 9

Adhesive Testing: The monomer was prepared and tested as described in Example 21. Adhesive strength was ~25 grams/0.5 inch at 5 minutes.

EXAMPLE 23

Bis-(4-isocyanatobenzoyl-polyglycolyl)-polyethylene glycol 200

This material was prepared exactly as per Example 20, except polyethylene glycol 400 (60.4 g., 0.151 mole) was substituted for diethylene glycol.

Adhesive Testing: This monomer was prepared and tested as described in Example 21. Adhesive strength=30 grams/0.5 inch at 3 minutes.

EXAMPLE 26

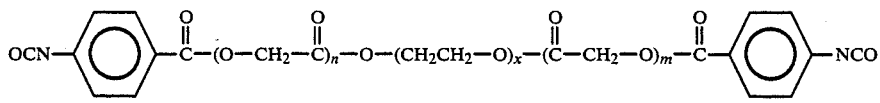

Where n + m ≈ 4 and x ≈ 4

Bis-(4-isocyanatobenzoyl-polyglycolyl)-diethylene glycol

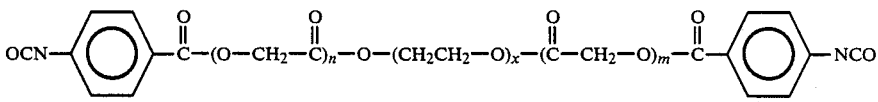

Where n + m ≈ 6 and x = 2

This material was prepared exactly as per Example 20, except the glycolide was increased to 5/grams, 0.440 mole.

Adhesive Testing: This monomer was prepared and tested as described in Example 21. Adhesive strength ≈100 grams/0.5 inch at 1 minute.

EXAMPLE 27

Bis-(4-isocyanatobenzoyl-polyglycolyl)-polyethylene glycol 600

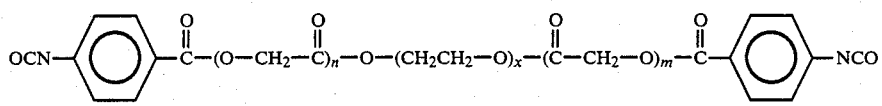

Where n + m ≈ 6 and x ≈ 13

This material was prepared as per Example 22, except the glycolide was increased by 50%.

Adhesive Testing: This monomer was prepared and tested as described in Example 21. Adhesive strength ≈25 grams/0.5 inch at 4 minutes.

EXAMPLE 28

Bis-(4-isocyanatobenzoyl-polylactoyl)-diethylene glycol

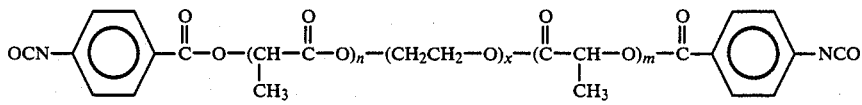

Where n + m ≈ 4 and x = 2

This material was prepared as per the procedure of Example 20, except that lactide was substituted for glycolide.

Adhesive Testing: This monomer was prepared and tested as described in Example 21. Adhesive strength ≈40 grams/0.5 inch after three minutes. With 50% more catalyst, adhesive strength was 100 grams/0.5 inch at 2 minutes.

EXAMPLE 29

Bis-(4-isocyanatobenzoyl-polyglycolyl)-dipropylene glycol

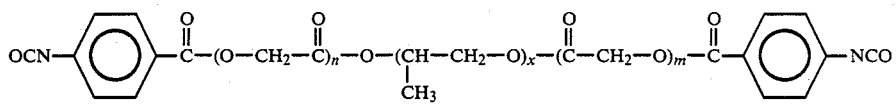

Where n + m ≈ 4 and x = 2

This material was prepared exactly as described in Example 20, except that dipropylene glycol was substituted for diethylene glycol.

Adhesive Testing: This monomer was tested as described in Example 21. Adhesive strength ≈118 grams/0.5 inch after one minute.

EXAMPLE 30

Bis-(4-isocyanatobenzoyl-polyglycolyl)-polypropylene glycol 725

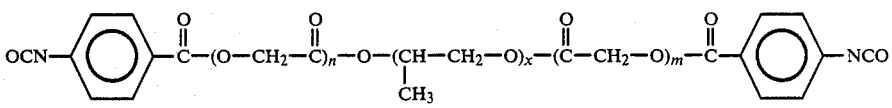

Where n + m ≈ 4 and x ≈ 12

This material was prepared as described in Example 22, except polypropylene glycol 725 was substituted for polyethylene glycol 600.

Adhesive Testing: This monomer was tested as described in Example 21. Adhesive strength=40 grams/0.5 inch at 5 minutes.

EXAMPLE 31

Bis-(4-isocyanatobenzoyl-polyglycolyl)-ethylene glycol

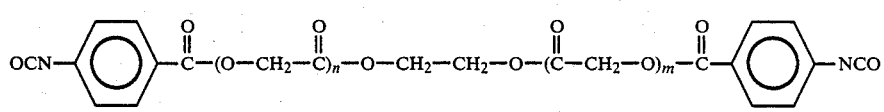

Where n + m ≈ 4

This material was prepared according to the procedure of Example 20, except that ethylene glycol was substituted for diethylene glycol.

Adhesive Testing: This monomer was prepared and tested as described in Example 21. Adhesive strength ≈159 grams/0.5 inch at 1 minute.

EXAMPLE 32

Bis-(4-isocyanatobenzoyl-polyglycolyl-lactoyl)-diethylene glycol

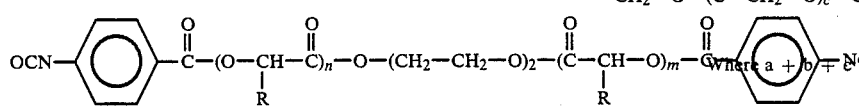

This material was prepared according to the procedure of Example 20, except that a 50/50 mixture of lactide and glycolide was substituted for the glycolide.

Adhesive Testing: This monomer was prepared and tested as described in Example 21. Adhesive strength ≈90 gram/0.5 inch at 1 minute.

EXAMPLE 33

Tris-(4-isocyanatobenzoyl-polyglycolyl)-glycerol

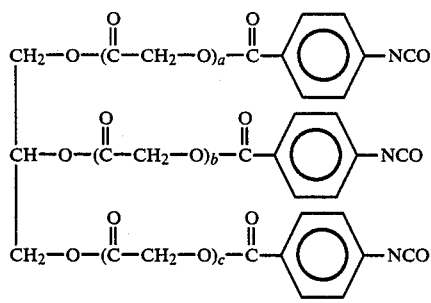

Where a + b + c ≈ 5

This material was prepared according to the procedure of Example 20, except that glycolide (83.0 grams, 0.5 mole) and glycerol (7.5 g., 0.082 mole) in place of diethylene glycol, were used in part A. This product was reacted with 4-nitrobenzoyl chloride (54.7 g., 0.295 mole) and 4-dimethylamino pyridine (43.2 g., 0.354 mole) in part B. The triisocyanate was obtained as an amber glass.

Adhesive Testing: This monomer was prepared and tested as described in Example 21. Adhesive strength ≈85 grams/0.5 inch after one minute.

EXAMPLE 34

Tris-(4-isocyanatobenzoyl-polyglycolyl)-glycerol

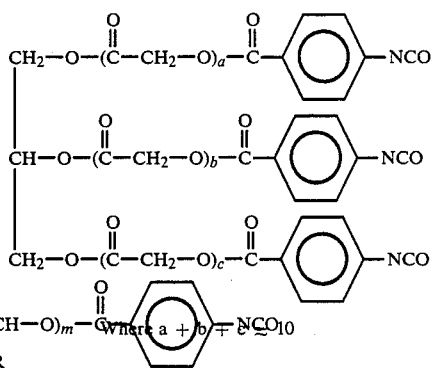

This material was prepared as per Example 33, except double the amount of glycolide was used.

Adhesive Testing: This monomer was prepared and tested as described in Example 21. Adhesive strength ≈80 grams/0.5 inch at 1 minute.

EXAMPLE 35

Tris-(4-isocyanatobenzoyl-polyglycolyl)-trimethylol propane

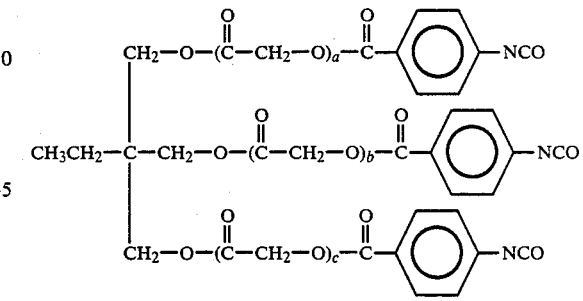

Where a + b + c ≈ 6

This material was prepared by the procedure of Example 33, except trimethol propane was substituted for glycerol and the glycolide was increased to give a+b+c=6.

Adhesive Testing: This monomer was prepared for testing as described in Example 21. Adhesive strength ≈80 grams/0.5 inch after one minute.

EXAMPLE 36

Tris-(4-isocyanatobenzoyl-polyglycolyl)-ethyleneglycoltrimethanol propane

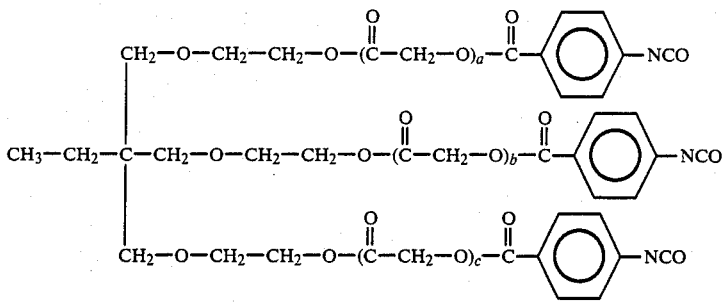

(Where a + b + c = 6)

This material was prepared by chain extending trimethol propane with ethylene oxide and reacting the resulting triol as described in Example 35.

Adhesive strength=105 grams/0.5 inch at 1 minute.

EXAMPLE 37

Diglycolyl-bis-(ethyl-4-isocyanato benzoate)

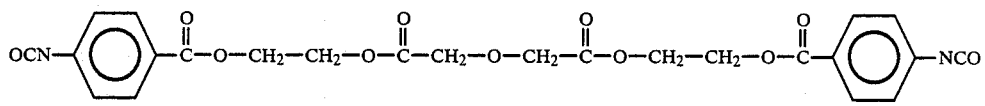

A. Ethylene carbonate (20 g., 0.22 mole), 4-Nitrobenzoic acid (38 g., 0.2 mole), and tetraethylammonium chloride (2.0 g., 0.04 mole) were placed in a one liter round bottom flask and heated at 140° C. with stirring until evolution of $CO_2$ stopped. The reaction was cooled to room temperature and dissolved in one liter of ethyl acetate. The solution was washed with water and dried over $MgSO_4$. The drying agent was removed by filtration. The volume was reduced in-vacuo and the 2-hydroxyethyl-4-nitrobenzoate obtained as a pale yellow solid. The structure was confirmed by NMR spectroscopy.

B. Diglycolic acid (13.4 g., 0.1 mole) was slurried in chloroform (150 ml.) and phosphorous pentachloride (45 g., 0.22 mole) added all at once. The mixture was slowly brought to reflux over about one hour. Reflux was maintained for 1.5 hours. After cooling the chloroform was removed under reduced pressure (20 mm) and the phosphorous oxy-chloride, which had formed, was removed by distillation at 0.5 mm Hg (~25° C.). The product (diglycolyl chloride) was collected at 56°–57° C. and 0.5 mm Hg. Structure was confirmed by IR and NMR spectroscopy.

C. Diglycolyl chloride (8.5 g., 0.05 mole) and 2-Hydroxylethyl-4-nitrobenzoate were condensed as described in Example 20, part B. The resulting di-nitro material was converted to the di-isocyanate by the procedure of Example 20 (Part C and D).

Adhesive Testing: This monomer was tested as described in Example 21. Adhesive strength ≈115 grams/0.5 inch at 1 minute.

EXAMPLE 38

Dimalonyl-bis-(ethyl-4-isocyanato-benzoate)

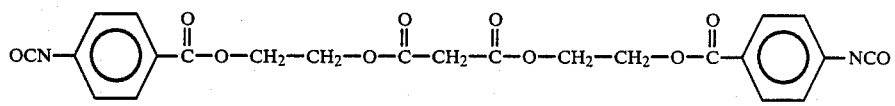

This material was prepared according to the procedure of Example 37, except malonyl dichloride was substituted for diglycolyl dichloride.

Adhesive Testing: This monomer was tested as described in Example 2. Adhesive strength=165 grams/0.5 inch at two minutes (on hydrated cellulose).

EXAMPLE 39

Oxalyl-bis-(ethyl-4-isocyanatobenzoate)

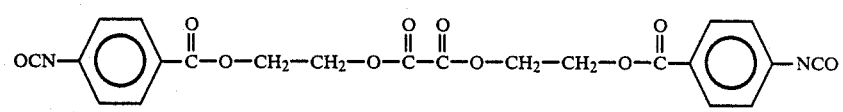

This material was prepared by the procedure of Example 37, except oxalyl chloride was substituted for diglycolyl dichloride.

Adhesive Testing: This monomer was tested according to the procedure of Example 2. Adhesive strength=30 grams/0.5 inch at 4 minutes (on hydrated cellulose).

EXAMPLE 40

Oxalyl-bis-(propyl-4-isocyanato-benzoate)

EXAMPLE 43

Bis-(4-isocyanatobenzoyl-glycolyl)-ethylene glycol

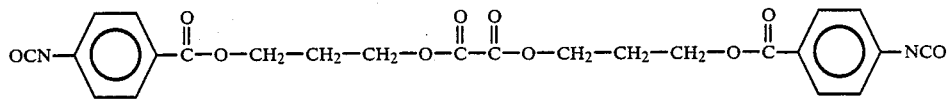

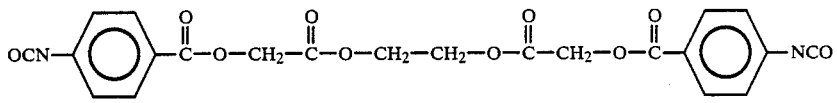

This material was prepared according to Example 37, except propylene carbonate was substituted for ethylene carbonate and oxalyl chloride was substituted for diglyolyl dichloride.

Adhesive Testing: This monomer was tested by the procedure of Example 21. Adhesive strength (on rat skin)=83 grams/0.5 inch at 1 minute.

EXAMPLE 41

Bis-(4-isocyanatobenzoyl)-polypropyloxalate

4-Aminobenzoic acid was condensed with t-butyloxydicarbonate by standard procedure to give t-butyloxycarbonyl-4-amino-benzoic acid. This was condensed (by the action of carbonyldiimidazole) with glycolic acid benzyl ester. The benzyl ester was removed by hydrogenation (Pd/C) and the resulting acid reacted with 1,2-dichloroethane to give bis-(t-butyloxycarbonyl-4-amino-benzoylglycolyl)-ethylene glycol. The t-butyloxycarbonyl group was removed with HCl/dioxane, and the diamine converted to the diisocyanate.

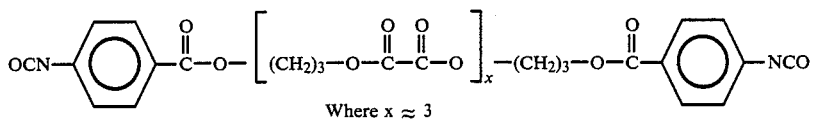

Where x ≈ 3

Oxalyl chloride was condensed (without solvent) with 1,3-propane diol to give the corresponding diol where x=3. This diol was carried through to the diisocyanate by the procedure of Example 20.

Adhesive Testing: This monomer was tested according to the procedure of Example 21. Adhesive strength ≈38 grams/0.5 inch at 1 minute.

EXAMPLE 42

Bis-(4-isocyanatobenzoyl-hydroxy-ethyl-glycolate)-diethylene glycol ether

Adhesive Testing: This monomer was tested according to the procedure of Example 21. Adhesive strength=15 grams/0.5 inch at 2 minutes.

EXAMPLE 44

Bis-(4-isocyanatobenzoyl-glycolyl)-diethylene glycol

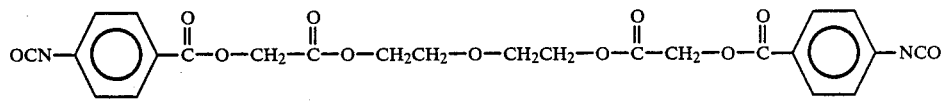

This material was prepared according to the procedure of Example 43, except that 2-chloroethyl ether was substituted for 1,2-dichloroethane.

Adhesive Testing: This monomer was tested according to the procedure of Example 21. Adhesive

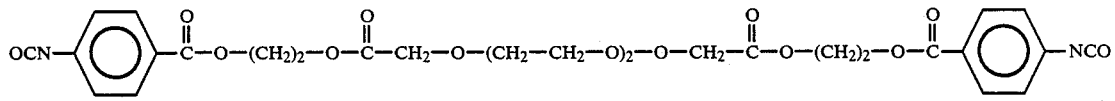

Tetraethylene glycol was oxidized to the corresponding diiacid, converted to the acid chloride by the reaction of thionyl chloride and condensed with 2-hydroxyethyl-4-nitrobenzoate. The latter was then converted to the diisocyanate according to the procedures of Example 37.

Adhesive Testing: This monomer was tested by the procedure of Example 21. Adhesive strength=112 grams/0.5 inch at 1 minute.

strength=103 gram/0.5 inch at 1 minute.

EXAMPLE 45

Adhesive Composition

An adhesive composition was prepared by mixing 85% by weight of the monomer of Example 20 with 15% by weight of the monomer of Example 33, and performing adhesive testing as described in Example 21. Adhesive strength >200 grams/0.5 inch at 1 minute.

EXAMPLE 46

Adhesive Composition

An adhesive composition was prepared by mixing 60% by weight of the monomer of Example 22 with 40% by weight of the monomer of Example 33, and performing adhesive testing as described in Example 21. Adhesive strength >200 grams/0.5 inch at 1 minute.

EXAMPLE 47

Adhesive Composition

An adhesive composition was prepared by mixing 70% by weight of the monomer of Example 24 with 30% by weight of the monomer of Example 33, and performing adhesive testing as described in Example 21. Adhesive strength >200 grams/0.5 inch at 1 minute.

EXAMPLE 48

Adhesive Composition

An adhesive composition was prepared by mixing 70% by weight of the monomer of Example 1 with 30% by weight of the monomer of Example 33, and performing adhesive testing as described in Example 21. Adhesive strength 200 grams/0.5 inch at 1 minute.

(The monomer from Example 1 under these conditions gives an adhesive strength of 110 grams/0.5 inch at 1 minute.)

EXAMPLE 49

Adhesive Composition

As Example 45, except dissolve monomer in methylene chloride. Adhesive strength = 175 grams/0.5 inch at 2 minutes.

EXAMPLE 50

Adhesive Composition Spray

The monomers from Example 22 and 33 were mixed in a ratio of 60/40 (wt./wt.) and dissolved in cold dichlorofluoromethane at a concentration of 25% (wt./wt.). 60 $\mu$l of triethylamine per gram of monomer was added and the solution placed in a pressure bottle equipped with an aerosol spray nozzle. The solution was allowed to warm to room temperature and the adhesive solution sprayed onto the substrate. An adhesive strength of greater than 200 grams/0.5 inch at 1 minute (rat skin) was obtained.

EXAMPLE 51

Curing Agents

The diol from part A of Example 20 was mixed with the adhesive composition of Example 46 in a molar ratio of 0.2/1 (diol/isocyanate) and tested as described in Example 21. Adhesive strength ≈ 175 grams/0.5 inch at 2 minutes.

EXAMPLE 52

Absorption of Polymers Derived from Adhesive Monomers (in-vitro)

Each monomer or monomer mixture was prepared as described in Example 20. Each solution was spread over the surface of a glass slide and allowed to polymerize in the presence of 90+% humidity for 24 hours. The resulting polymers are dried under vacuum and scraped off the slides. The polymers are incubated in 0.1 M phosphate buffer pH 7.4 (seal tubes) for various times and temperatures. After each time interval the polymer left unadsorbed was collected and weighed. The results are given as wt. % of polymer remaining as a function of time and temperature. The results are summarized in Table 4.

TABLE 4

ABSORPTION STUDIES

| Polymer Derived From Monomer of Example | Wt. % Remaining | Time | Temp. |
| --- | --- | --- | --- |
| 1 | 84 | 94 hours | 99° C. |
| 20 | 34 | 7 hours | 99° C. |
|  | 7 | 24 hours | 99° C. |
|  | 1.3 | 48 hours | 99° C. |
|  | 0.8 | 71 hours | 99° C. |
|  | 0.0 | 98 hours | 99° C. |
|  | 93 | 14 days | 50° C. |
|  | 15 | 39 days | 50° C. |
|  | 14 | 70 days | 50° C. |
|  | 0.0 | 6 months | 50° C. |
| 20/33 (80/20) | 35 | 12 hours | 99° C. |
|  | 2 | 65 hours | 99° C. |
|  | 0.0 | 87 hours | 99° C. |
|  | 58 | 32 days | 50° C. |
|  | 12 | 60 days | 50° C. |
|  | 53 | 8 days | 50° C. |
|  | 24 | 14 days | 50° C. |
|  | 8 | 22 days | 50° C. |
|  | 38 | 60 days | 37° C. |
|  | 22 | 127 days | 37° C. |
| 22/33 (60/40) | 70 | 60 days | 37° C. |
|  | 5 | 96 days | 37° C. |
| 23 | 83 | 2 days | 50° C. |
|  | 59 | 7 days | 50° C. |
|  | 30 | 14 days | 50° C. |
| 28 | 81 | 7 hours | 99° C. |
|  | 73 | 24 hours | 99° C. |
|  | 53 | 48 hours | 99° C. |
|  | 46 | 72 hours | 99° C. |
|  | 32 | 98 hours | 99° C. |
|  | 91 | 39 days | 50° C. |
| 28 | 62 | 6 months | 50° C. |
|  | 85 | 7 days | 50° C. |
|  | 85 | 14 days | 50° C. |
| 33 | 1.9 | 12 hours | 99° C. |
|  | 0.0 | 65 hours | 99° C. |
|  | 92 | 31 days | 50° C. |
|  | 1.4 | 60 days | 50° C. |
| 37 | 22 | 87 hours | 99° C. |
|  | 92 | 39 days | 50° C. |
|  | 80 | 77 days | 50° C. |
|  | 40 | 6.5 months | 50° C. |
| 39 | 0.0 | 8 days | 50° C. |
| 40 | 67 | 7 days | 50° C. |
|  | 71 | 14 days | 50° C. |
|  | 70 | 44 days | 50° C. |
| 41 | 37 | 7 days | 50° C. |
|  | 41 | 14 days | 50° C. |
|  | 44 | 43 days | 50° C. |
| 42 | 37 | 26 hours | 99° C. |
|  | 85 | 30 days | 50° C. |
| 43 | 71 | 7 hours | 99° C. |
|  | 42 | 24 hours | 99° C. |
|  | 32 | 47 hours | 99° C. |
|  | 20 | 72 hours | 99° C. |
|  | 13 | 94 hours | 99° C. |
| 44 | 72 | 7 hours | 99° C. |
|  | 49 | 24 hours | 99° C. |
|  | 22 | 47 hours | 99° C. |
|  | 4.8 | 72 hours | 99° C. |
|  | 5.4 | 94 hours | 99° C. |
|  | 84 | 30 days | 50° C. |

It is claimed:
1. A method of closing a wound in living tissue which comprises applying to the tissues to be bonded together a curable surgical adhesive comprised of
A. a metabolically-acceptable polyisocyanate having the structural formula:

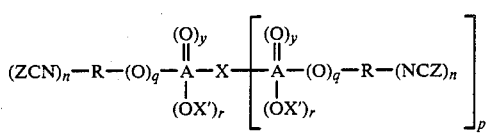

wherein
R is a polyvalent aliphatic radical of about 1 to 10 carbon atoms or a polyvalent aromatic radical of 6 to about 24 carbon atoms;
A is carbon, sulfur or phosphorus;
Z is oxygen or sulfur;
y is 1 when A is carbon or phosphorus, and 2 when A is sulfur;
n is 1 or 2;
p is at least 1;
q is 0 or 1, with the proviso that when A is carbon or sulfur, q is 0;
r is 0 or 1, with the proviso that when A is carbon or sulfur, r is 0; and
X is the residue of an organic compound having terminal active hydrogen-containing groups, and
X' is a residue of an organic compound having at least 1 active hydrogen-containing group; or
B. an excess of said polyisocyanate A above in admixture with an organic compound containing at least two active hydrogen atoms reactive with the polyisocyanate.

2. A method according to claim 1 wherein the curable surgical adhesive comprises a metabolically-acceptable polyisocyanate having the structure:

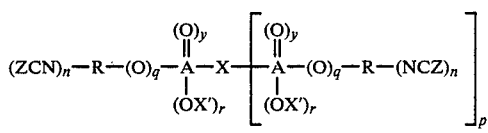

wherein
R is a polyvalent aliphatic radical of about 1 to 10 carbon atoms or a polyvalent aromatic radical of 6 to about 24 carbon atoms;
A is carbon, sulfur or phosphorus;
Z is oxygen or sulfur;
y is 1 when A is carbon or phosphorus, and 2 when A is sulfur;
n is 1 or 2;
p is at least 1;
q is 0 or 1, with the proviso that when A is carbon or sulfur, q is 0;
r is 0 or 1, with the proviso that when A is carbon or sulfur, r is 0; and
X is the residue of an organic compound having terminal active hydrogen-containing groups; and
X' is a residue of an organic compound having at least 1 active hydrogen-containing group.

3. A method according to claim 1 wherein the curable surgical adhesive comprises an excess of said polyisocyanate from A above in admixture with an organic compound containing at least two active hydrogen atoms reactive with the polyisocyanate.

4. A method according to claim 1 or 2 wherein the curable surgical adhesive includes a catalyst.

5. A method according to claim 4 wherein the catalyst is a tertiary amine.

6. A method according to claim 5 wherein the catalyst is selected from the group consisting of 1,2,4-trimethylpiperazine, N-methylmorpholine, triethylamine, N-(N,N-dimethylaminopropyl)2-pyrollidine, 2,4,6-collidine, pyridine, quinaldine, pyridazine, dibutyltindiacetate, stannous-2-ethylhexanoate, a pyridine carboxylate having the structure:

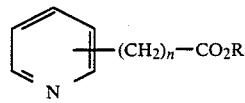

wherein R is lower alkyl, n is 0 to 6 or more; a piperidine carboxylate having the structure:

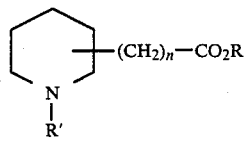

wherein R and n are as defined above, R' is lower alkyl; and an aliphatic amine having the structure:

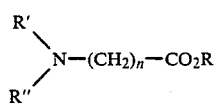

wherein R, R' and R'' are lower alkyl; n is as defined above; and an aliphatic amine having the structure:

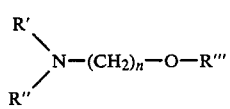

wherein R' is as defined above and R''' is hydrogen or

wherein R and n are as defined above.

7. A method according to claim 1 or 2 wherein in the structural formula, A is carbon and y is 1.

8. A method according to claim 1 or 2 wherein in the structural formula, A is sulfur and y is 2.

9. A method according to claim 1 or 2 wherein in the structural formula, A is phosphorus and y is 1.

10. A method according to claim 1 or 2 wherein in the structural formula, R is a divalent aromatic radical.

11. A method according to claim 1 or 2 wherein in the structural formula, the divalent aromatic radical is

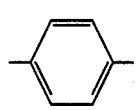

12. A method according to claim 1 or 2 wherein in the formula, the divalent aromatic radical is

13. A method according to claim 1 or 2 wherein in the structural formula, n is 1.

14. A method according to claim 1 or 2 wherein in the structural formula, n is 2.

15. A method according to claim 1 or 2 wherein in the structural formula, X is the residue of a hydroxy-terminated polymer.

16. A method according to claim 15 wherein the hydroxy-terminated polymer is a polymeric polyol.

17. A method according to claim 16 wherein the polymeric polyol residue is selected from a group consisting of polyester polyol, polyether polyol and polyether/polyester residues.

18. A method according to claim 17 wherein the polymeric polyol residue is a polyester polyol residue.

19. A method according to claim 18 wherein the polyester polyol residue has the structure:

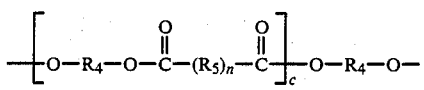

or

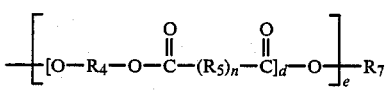

wherein $R_4$ and $R_5$ are aliphatic or aromatic radicals having 1 to 12 carbon atoms; $R_7$ is a polyfunctional active hydrogen-containing aliphatic radical; n is an integer of 0 or 1; c and d are integers of at least 1; and e is an integer of at least 2.

20. A method according to claim 18 wherein the polyester polyol residue has the structure:

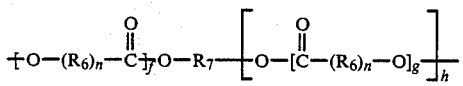

wherein $R_6$ is an aliphatic or aromatic radical having 1 to 12 carbon atoms; $R_7$ is a polyfunctional active hydrogen-containing aliphatic radical; n is an integer of 0 or 1; and f, g, and h are integers of at least 1.

21. A method according to claim 17 wherein the polymeric polyol residue is a polyether polyol residue.

22. A method according to claim 21 wherein the polyether polyol residue has the structure:

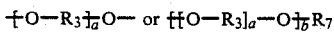

wherein $R_3$ is an aliphatic or aromatic radical of 1 to 12 carbon atoms; $R_7$ is a polyfunctional active hydrogen-containing aliphatic radical; a is an integer of at least 1; and b is an integer of at least 2.

23. A method according to claim 17 wherein the polymeric polyol residue is a polyether/polyester polyol copolymer residue.

24. A method according to claim 23 wherein the polyether/polyester polyol copolymer residue has the structure:

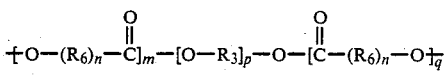

or

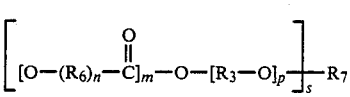

wherein $R_3$ and $R_6$ are aliphatic or aromatic radicals of 1 to 12 carbon atoms; $R_7$ is a polyfunctional active hydrogen-containing aliphatic radical; m, p, and q are integers of at least 1; and s is an integer of at least 2.

25. A method according to claim 1 or 2 wherein X in the structural formula is the residue of a polymer containing hydrolyzable linkages.

26. A method according to claim 1 or 2 wherein X in the structural formula is the residue of a polymer susceptible to cleavage by proteolytic enzymes.

27. A method according to claim 1 or 2 wherein the polyisocyanate has the formula:

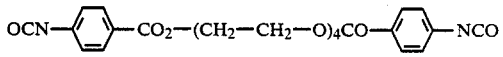

28. A method according to claim 1 or 2 wherein the polyisocyanate has the formula:

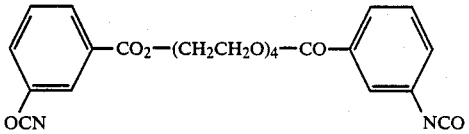

29. An article of manufacture comprising a two container pack for providing, on mixing of the two components of the pack, a surgical adhesive, which two container pack comprises: in a first container a curable, sterile, polyisocyanate as defined in claim 2 and in a second container an organic compound containing at least two active hydrogen atoms reactive with isocyanate groups of the polyisocyanate, the amount of the polyisocyanate in the first container being in excess of the organic compound in the second container.

30. The article of manufacture of claim 29 wherein the components in at least one of the containers includes one or more curing catalysts.

31. An article of manufacture comprising a container for delivering a single-component surgical adhesive which comprises a formulation of at least 1 curable, sterile, polyisocyanate as defined in claim 2.

32. The article of manufacture of claim 31 wherein the container is a spray container.

33. An article of manufacture comprising a two container pack for providing on mixing of the two components of the pack, a rapid curing surgical adhesive, which two container pack comprises: in a first container a formulation of at least 1 curable, sterile, polyisocyanate as defined in claim 2 and in a second container a curing catalyst for said polyisocyanate.

34. The article of manufacture of claim 33 wherein the two component pack is a two component spray.

35. The articles of manufacture of claims 29, 30, 31, 32, 33, and 34 wherein one or all of the components are dissolved in an appropriate solvent.

36. The article of manufacture of claim 35 wherein the solvent is dichlorofluoromethane.

37. A composition comprising a polyisocyanate having the structural formula:

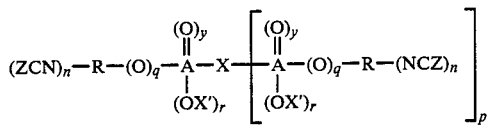

wherein R is a polyvalent aliphatic radical of about 1 to 10 carbon atoms or a polyvalent aromatic radical of 6 to about 24 carbon atoms;
  A is carbon, sulfur or phosphorus:
  Z is oxygen or sulfur;
  y is 1 when A is carbon or phosphorus, and 2 when A is sulfur;
  n is 1 or 2;
  p is at least 1;
  q is 0 or 1, with the proviso that when A is carbon or sulfur, 1 is 0;
  r is 0 or 1, with the proviso that when A is carbon or sulfur, r is 0;
  X is the residue of a hydroxy-terminated polyester or polyether/polyester; and
  X' is the residue of an organic compound having at least 1 active hydrogen-containing group.

38. A polyisocyanate according to claim 37 wherein the polyester polyol residue has the structure:

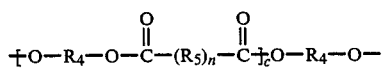

or

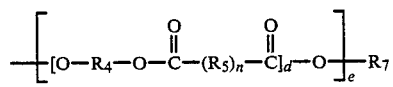

wherein $R_4$ and $R_5$ are aliphatic or aromatic radicals having 1 to 12 carbon atoms; $R_7$ is a polyfunctional active hydrogen-containing aliphatic radical; n is an integer of 0 to 1; c and d are integers of at least 1; and e is an integer of at least 2.

39. A polyisocyanate according to claim 37 wherein the polyester polyol residue has the structure:

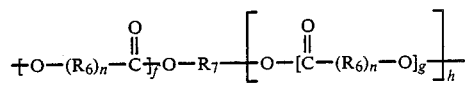

wherein $R_6$ is an aliphatic or aromatic radical having 1 to 12 carbon atoms; $R_7$ is a polyfunctional active hydrogen-containing aliphatic radical; n is an integer of 0 or 1; and f, g, and h are integers of at least 1.

40. A polyisocyanate according to claim 37 wherein the polyether/polyester polyol copolymer residue has the structure:

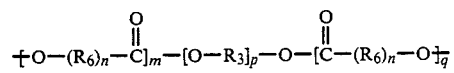

or

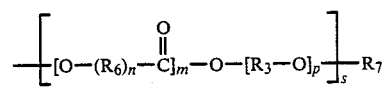

wherein $R_3$ and $R_6$ are aliphatic radicals of 1 to 12 carbon atoms or aromatic radicals of 6 to 12 carbon atoms; $R_7$ is a polyfunctional active hydrogen-containing aliphatic radical; n is an integer of 0 or 1; m, p, and q are integers of at least 1; and s is an integer of at least 2.

41. A curable polyisocyanate according to claim 40 wherein $R_3$ is —$CH_2$—$CH_2$—, $R_6$ is —$CH_2$— and n is 1.

42. A curable polyisocyanate according to claim 41 wherein the polyisocyanate has the structure:

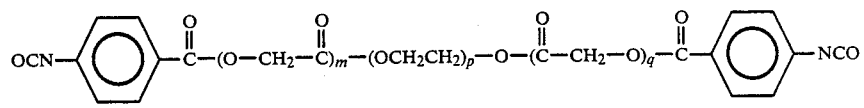

wherein m is 1 to 10; p is 1 to 20 and q is 1 to 10.

43. A polyisocyanate according to claim 39 wherein $R_6$ is —$CH_2$—, $R_7$ is a triol, and n is 1.

44. A curable polyisocyanate according to claim 43 having the structure:

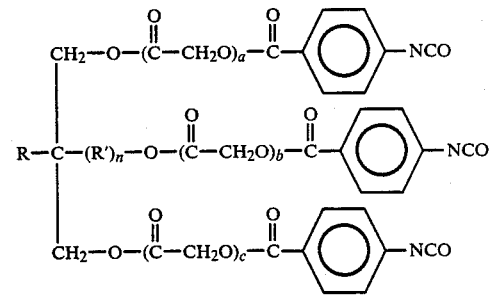

wherein
  R is hydrogen or lower alkyl;
  R' is an alkylene of 1 to 4 carbon atoms;
  n is 1 or 1; and
  a+b+c is at least 3.

45. A curable polyisocyanate composition comprising a mixture of 5 to 95% by weight of a polyisocyanate I having the structure:

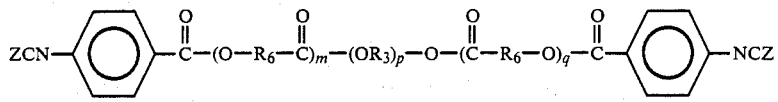

and 5 to 95% of a polyisocyanate II having the structure:

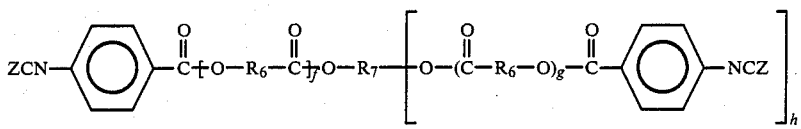

wherein $R_3$ and $R_6$ are aliphatic or aromatic radicals having 1 to 12 carbon atoms; $R_7$ is a polyfunctional active hydrogen-containing aliphatic radical; f, g, h, m, p, and q are integers of at least 1; and Z is oxygen.

46. A curable polyisocyanate composition according to claim 45 wherein polyisocyanate I has the structure:

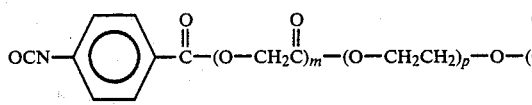

wherein m is 1 to 10; p is 1 to 20, and q is 1 to 10; and polyisocyanate II has the structure:

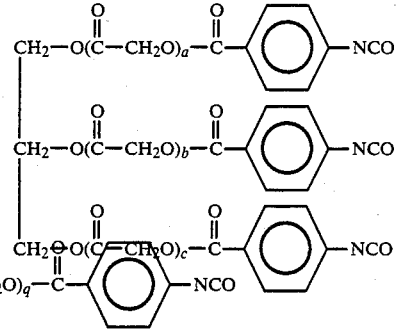

wherein $a+b+c$ is at least 3.

47. A curable polyisocyanate composition according to claim 46 comprising about 5 to 95% of polyisocyanate I and about 5 to 95% by weight of polyisocyanate II.

* * * * *